US012624040B2

(12) United States Patent
Liu et al.

(10) Patent No.: US 12,624,040 B2
(45) Date of Patent: May 12, 2026

(54) COMPOSITIONS OF SUBSTITUTED PYRAZOLOPYRIMIDINES AND USES THEREOF

(71) Applicant: KSQ Therapeutics, Inc., Lexington, MA (US)

(72) Inventors: Hanlan Liu, Lexington, MA (US); Robert M. Wenslow, Jr., Cream Ridge, NJ (US)

(73) Assignee: KSQ Therapeutics, Inc., Cambridge, MA (US)

( * ) Notice: Subject to any disclaimer, the term of this patent is extended or adjusted under 35 U.S.C. 154(b) by 879 days.

(21) Appl. No.: 17/792,472

(22) PCT Filed: Jan. 14, 2021

(86) PCT No.: PCT/US2021/013369

§ 371 (c)(1),
(2) Date: Feb. 7, 2023

(87) PCT Pub. No.: WO2021/146378

PCT Pub. Date: Jul. 22, 2021

(65) Prior Publication Data

US 2023/0065636 A1 Mar. 2, 2023

Related U.S. Application Data

(60) Provisional application No. 62/961,486, filed on Jan. 15, 2020.

(51) Int. Cl.

| | |
|---|---|
| ***C07D 487/04*** | (2006.01) |
| ***A61K 9/10*** | (2006.01) |
| ***A61K 9/16*** | (2006.01) |
| ***A61K 47/32*** | (2006.01) |
| ***A61K 47/38*** | (2006.01) |

(52) U.S. Cl.

CPC .............. *C07D 487/04* (2013.01); *A61K 9/10* (2013.01); *A61K 9/1682* (2013.01); *A61K 47/32* (2013.01); *A61K 47/38* (2013.01)

(58) Field of Classification Search

None

See application file for complete search history.

(56) References Cited

U.S. PATENT DOCUMENTS

| | | | |
|---|---|---|---|
| 5,010,175 | A | 4/1991 | Rutter et al. |
| 5,475,096 | A | 12/1995 | Gold et al. |
| 6,453,242 | B1 | 9/2002 | Eisenberg et al. |
| 7,964,356 | B2 | 6/2011 | Zichi et al. |
| 8,541,192 | B2 | 9/2013 | D'Andrea |
| 8,598,184 | B2 | 12/2013 | Zhang |
| 10,450,281 | B1 | 10/2019 | D'Andrea et al. |
| 2008/0318838 | A1 | 12/2008 | Bauer et al. |
| 2009/0062196 | A1 | 3/2009 | D'Andrea et al. |
| 2010/0190787 | A1 | 7/2010 | Kasibhatla et al. |
| 2011/0144134 | A1 | 6/2011 | Shokat et al. |
| 2012/0202690 | A1 | 8/2012 | Whittingham et al. |
| 2012/0252779 | A1 | 10/2012 | Ramsden et al. |
| 2013/0079512 | A1 | 3/2013 | Nagaraj et al. |
| 2013/0253005 | A1 | 9/2013 | D'Andrea et al. |
| 2017/0145012 | A1 | 5/2017 | Buckmelter et al. |
| 2017/0202810 | A1 | 7/2017 | D'Andrea et al. |
| 2021/0115049 | A1 | 4/2021 | Brenneman et al. |

FOREIGN PATENT DOCUMENTS

| | | | |
|---|---|---|---|
| CN | 106146511 | A | 11/2016 |
| WO | WO-9623899 | A1 | 8/1996 |
| WO | WO-9815833 | A1 | 4/1998 |
| WO | WO-2014105952 | A2 | 7/2014 |
| WO | WO-2015071474 | A2 | 5/2015 |
| WO | WO-2017026718 | A1 | 2/2017 |
| WO | WO-2020132269 | A1 | 6/2020 |
| WO | WO-2021146378 | A1 | 7/2021 |
| WO | WO-2022174184 | A1 | 8/2022 |

OTHER PUBLICATIONS

Audeh, M., et al., "Oral Poly (Adp-ribose) Polymerase Inhibitor Olaparib in Patients With BRCA1 or BRCA2 Mutations and Recurrent Ovarian Cancer: a Proof-of-concept Trial," Lancet 376(9737):245-251, Elsevier, Netherlands (Jul. 2010).

Beerli, R.R. and Barbas, C.F., "Engineering Polydactyl Zinc-finger Transcription Factors," Nature Biotechnology 20(2):135-141, Nature America Publishing, United States (Feb. 2002).

Berezovski, M.V., et al., "Aptamer-Facilitated Biomarker Discovery (AptabiD)," Journal of the American Chemical Society 130(28):9137-9143, American Chemical Society, Washington (2008).

Bingham, A.L., et al., "Over One Hundred Solvates of Sulfathiazole," Chemical Communications 7:603-604, Royal Society of Chemistry, United States (2001).

Bramsen, J.B and Kjems, J., "Chemical Modification of Small Interfering RNA," Methods of Molecular Biology 721:77-103, Springerlink, Germany (2011).

Bratkovic, T., et al., "Progress in Phage Display: Evolution of the Technique and Its Application," Cellular and molecular life sciences 67(5):749-767, Springer, Basel (2010).

Brody, N., et al., "High-Content Affinity-Based Proteomics: Unlocking Protein Biomarker Discovery," Expert review of molecular diagnostics 10(8):1013-1022, Taylor & Francis, United Kingdom (2010).

Cadzow, L., et al., "Development Of KSQ-4279 As A First-In-Class USP1 Inhibitor For the Treatment Of BRCA-Deficient Cancers," European Journal of Cancer 138(S2):S52, Abstract 184, 1 page, Elsevier, Netherlands (Oct. 2020).

(Continued)

*Primary Examiner* — Kamal A Saeed
*Assistant Examiner* — Quincy Mckoy
(74) *Attorney, Agent, or Firm* — Kilpatrick Townsend & Stockton LLP

(57) ABSTRACT

Pharmaceutical formulations comprising substituted pyrazolopyrimidines are disclosed herein. Also disclosed are amorphous solid dispersions comprising substituted pyrazolopyrimidines, processes for preparing these amorphous solid dispersions, pharmaceutical compositions comprising such dispersions, and methods of use thereof.

20 Claims, 23 Drawing Sheets

(56) References Cited

OTHER PUBLICATIONS

Caira, M,R., et al., "Preparation and Crystal Characterization of a Polymorph, a Monohydrate, and an Ethyl Acetate Solvate of the Antifungal Fluconazole," Journal of Pharmaceutical Sciences 93(3):601-611, American Pharmaceutical Association, United States (2004).
Chan, J.H.P., et al., "Antisense Oligonucleotides: From Design to Therapeutic Application," Clinical and Experimental Pharmacology 33(5-6):533-540, Wiley Online Library, United States (May-Jun. 2006).
Chaturvedi, K., et al., "Cyclodextrin-Based siRNA Delivery Nanocarriers: a State-of-The-Art Review," Expert Opinion on Drug Delivery 8(11):1455-1468, Informa Healthcare, United Kingdom (2011).
Chen, J., et al., "Selective and Cell-Active Inhibitors of the USP1/UAF1 Deubiquitinase Complex Reverse Cisplatin Resistance in Non-small Cell Lung Cancer Cells," Chem. Biol. 18(11):1390-1400, Elsevier, Netherlands (2011).
Chernolovskaya, L., et al., "Chemical Modification of siRNA," Molecular therapeutics 12(2):158-167, Thomson Reuters (Scientific) Ltd, United Kingdom (2010).
Choo, Y. and Isalan, M., "Advances in Zinc Finger Engineering," Current Opinion in Structural Biology 10(4):411-416, Elsevier Science, United Kingdom (Aug. 2000).
Chylinski, K., et al., "The TracrRNA and Cas9 Families of Type II CRISPR-Cas Immunity Systems," RNA Biology 10(5):726-737, Taylor & Francis, United States (May 2013).
Davis, M., et., "Ubiquitin-Specific Proteases As Druggable Targets," Drug target review 2(3):60-64, Russell Publishing Ltd, United Kingdom (2015).
Deveau, H., et al., "Phage Response to CRISPR-Encoded Resistance in *Streptococcus thermophilus*," Journal of Bacteriology 190(4):1390-1400, American Society for Microbiology, United States (Feb. 2008).
Dolomanov, O. V., et al., "OLEX2: a complete structure solution, refinement and analysis program," Journal of Applied Crystallography 42(2):339-341, International Union of Crystallography, United Kingdom (Apr. 2009).
Ellington, A., et al., "In vitro selection of RNA molecules that bind to specific ligands," Nature 346(6287):818-822, Nature Publishing Group, Germany (1990).
Esvelt, K.M., et al., "A System for the Continuous Directed Evolution of Biomolecules," Nature 472(7344):499-503, Nature Publishing Group, United Kingdom (Apr. 2011).
Esvelt, K.M., et al., "Orthogonal Cas9 Proteins for RNA-guided Gene Regulation and Editing," Nature Methods 10(11):1116-1121, Nature Publishing Group, United States (Nov. 2013).
Farrugia, L. J., "WinGX and ORTEP for Windows: an update," Journal of Applied Crystallography 45(4):849-854, International Union of Crystallography, United Kingdom (Aug. 2012).
Fire, A., et al., "Potent and Specific Genetic Interference by Double-stranded RNA in Caenorhabditis Elegans," Nature 391(6669):806-811, Nature Publishing Group, United Kingdom (Feb. 1998).
Foged, C., "SiRNA Delivery With Lipid-Based Systems: Promises And Pitfalls," Current topics in medicinal chemistry 12(2):97-107, Bentham Science Publishers, United Arab Emirates (2012).
Fok, J. H. L., et al., "AZD7648 is a Potent and Selective DNA-PK Inhibitor That Enhances Radiation, Chemotherapy and Olaparib Activity," Nature Communications 10(1):5065, 15 pages, Nature Publishing Group, United Kingdom (Nov. 2019).
Gaglione, M., et al., "Recent progress in chemically modified siRNAS," Mini-reviews in medicinal chemistry 10(7):578-595, Bentham Science Publishers, United Arab Emirates (2010).
Gallop, M.A., et al., "Applications of combinatorial technologies to drug discovery. 1. Background and peptide combinatorial libraries," Journal of Medicinal Chemistry 37(9):1233-1251, American Chemical Society, United States (1994).
Gao, Y., et al., "Research Progress On SiRNA Delivery With Nonviral Carriers," International Journal of Nanomedicine 6:1017-1025, DOVE Medical Press, United States (2011).
Geary, R.S., "Antisense Oligonucleotide Pharmacokinetics and Metabolism," Expert opinion on drug metabolism and toxicology 5(4):381-391, Informa Healthcare, London (2009).
Gentilucci, L., et al., "Chemical Modifications Designed to Improve Peptide Stability: Incorporation of Non-Natural Amino Acids, Pseudo-Peptide Bonds, and Cyclization," Current pharmaceutical design 16(28):3185-3203, Bentham Science Publishers, United Arab Emirates (2010).
Horvath, P. and Barrangou, R., "CRISPR/Cas, the Immune System of Bacteria and Archaea," Science 327(5962):167-170, American Association for the Advancement of Science, United States (Jan. 2010).
Huang, T. T., and D'Andrea, A. D., "Regulation of DNA Repair by Ubiquitylation," Nature Reviews Molecular Cell Biology 7(5):323-334, Nature Publishing Group, United Kingdom (May 2006).
International Search Report and Written Opinion for Application No. PCT/US2021/57072, ISA/US, United States Patent and Trademark Office, United States, mailed on Feb. 18, 2022, 14 pages.
International Search Report and Written Opinion for Application No. PCT/US2021/13369, United States Patent and Trademark Office, United States, mailed on Mar. 31, 2021, 5 pages.
International Search Report and Written Opinion for International Application No. PCT/US19/67521, United States Patent and Trademark Office, United States, mailed on May 5, 2020, 14 pages.
Isalan, M., et al., "A Rapid, Generally Applicable Method to Engineer Zinc Fingers Illustrated by Targeting the HIV-1 Promoter," Nature Biotechnology 19(7):656-660, Nature America Publishing, United States (Jul. 2001).
Jacquemont, C., et al., "The Fanconi Anemia Pathway and Ubiquitin," BMC Biochemistry 8 Suppl 1(Suppl 1):S10, Biomed Central, United States (Nov. 2007).
Janssens, S., et al., "Review: Physical Chemistry of Solid Dispersions," J. Pharm. Pharmacol. 61(12):1571-1586, Oxford University Press, United Kingdom (Dec. 2009).
Kanasty, L., et al., "Action And Reaction: The Biological Response To SiRNA And Its Delivery Vehicles," Mol. Ther. 20(3):513-524, Cell Press, United States (2012).
Kim, J. M., et al., "Inactivation of Murine Usp1 Results in Genomic Instability and a Fanconi Anemia Phenotype," Developmental Cell 16(2):314-320, Cell Press, United States (Feb. 2009).
Kumari, A., et al., "Nanocarriers: a Tool To Overcome Biological Barriers In siRNA DELIVERY," Expert Opin. Biol. Ther. 11(10):1327-1339, Taylor & Francis, United States (2011).
Kurreck, J., "Antisense Technologies: Improvement Through Novel Chemical Modifications", European Journal of Biochemistry, 270(8):1628-1644, Blackwell Science Ltd. on behalf of the Federation of European Biochemical Societies, United Kingdom (2003).
Kurreck, J., et al., "Design of Antisense Oligonucleotides Stabilized by Locked Nucleic Acids," Nucleic Acids Research 30(9):1911-1918, Oxford University Press, United Kingdom (May 2002).
Lee, S.K., et al., "Cell-Specific SiRNA Delivery by Peptides and Antibodies," Meth. Enzymol. 502:91-122, Academic Press, United States (2012).
Liang, Q., et al., "A Selective USP1-UAF1 Inhibitor Links Deubiquitination To DNA Damage Responses," Nature 10(4):298-304, Nature Publishing Group, United Kingdom (2014).
Lim, K.S., et al., "Abstract 333: USP1 is required for replication fork stability in BRCA1-deficient tumors," AACR 78(13): 1 page, Proceedings of the American Association for Cancer Research Annual Meeting, Apr. 14-18, United States (2018).
Lord, C. J., and Ashworth, A., "PARP inhibitors: Synthetic Lethality in the Clinic," Science 355(6330): 1152-1158, American Association for the Advancement of Science, United States (Mar. 2017).
Macrae, C. F., et al., "Mercury: visualization and analysis of crystal structures," Journal of Applied Crystallography 39(3):453-457, International Union of Crystallography, United Kingdom (Jun. 2006).
Mali, P., et al., "RNA-Guided Human Genome Engineering via Cas9," Science 339(6121):823-826, American Association for the Advancement of Science, United States (Feb. 2013).
Mcmanus, M.T., et al., "Gene Silencing In Mammals By Small Interfering RNAs," Nat Rev Genet 3:737-747, Nature Publishing Group, United Kingdom (Oct. 2002).

(56) References Cited

OTHER PUBLICATIONS

Miller, J., et al., "Repetitive Zinc-Binding Domains in the Protein Transcription Factor IIIA from Xenopus Oocytes," The EMBO journal 4(6):1609-1614, Wiley-Blackwell, United Kingdom (Jun. 1985).
Mistry, H., et al., "Small-Molecule Inhibitors of USP1 Target ID1 Degradation in Leukemic Cells," Molecular cancer therapeutics 12(12):2651-2662, American Association for Cancer Research Inc., United States (2013).
Murai, J., et al., "The USP1/UAF1 Complex Promotes Double-Strand Break Repair Through Homologous Recombination," Molecular and Cellular Biology 31(12):2462-2469, American Society for Microbiology, United States (Jun. 2011).
Naeye, B., et al., "Matrix Systems for siRNA Delivery," Current Topics in Medicinal Chemistry, 12(2):89-96, Bentham Science Publishers, United Arab Emirates (2012).
Ni, X., et al., "Nucleic Acid Aptamers: Clinical Applications And Promising New Horizons," Current Medicinal Chemistry 18(27):4206-4214, Bentham Publishers, United Arab Emirates (2011).
Pabo, C.O., et al., "Design And Selection Of Novel Cys2His2 Zinc Finger Proteins," Annual Review of Biochemistry 70:313-340, Annual Reviews, United States (2001).
Pande, J., et al., "Phage Display: Concept, Innovations, Applications and Future," Biotechnology Advances 28(6):849-858, Elsevier, Netherlands (Nov.-Dec. 2010).
Parmar, K., et al., "Hematopoietic Stem Cell Defects in Mice With Deficiency of Fancd2 or Usp1," Stem Cells 28(7):1186-1195, Oxford University Press, United Kingdom (Jul. 2010).
Pasternak, A and Wengel, J., "Unlocked Nucleic Acid—An RNA Modification With Broad Potential," Organic & Biomolecular Chemistry (9):3591-3597, Royal Society of Chemistry, United Kingdom (2011).
Peacock, H., et al., "Chemical Modification of siRNA Bases to Probe and Enhance RNA Interference," The Journal of Organic Chemistry, 76(18):7295-7300, ACS Publications, United States (2011).
Prakash, T.P., "An Overview of Sugar-Modified Oligonucleotides for Antisense Therapeutics," Chemistry & Biodiversity 8(9):1616-1641, Wiley-Blackwell, United States (Sep. 2011).
PubChem, "SID 38205792," pubchem.ncbi.nlm.nih.gov, Deposit Date: Dec. 5, 2007, accessed at URL:[https://pubchem.ncbi.nlm.nih.gov/substance/38205792].
Pubchem CID 129736955,9-Benzyl-2-(o-fluorophenyl)purine, Sep. 13, 2017, accessed at https://pubchem.ncbi.nlm.nih.gov/compount/129736955, accessed on Feb. 12, 2020.
Rageul, J., and Kim, H., "Fanconi Anemia and the Underlying Causes of Genomic Instability," Environmental and Molecular Mutagenesis 61(7):693-708, Wiley, United States (Aug. 2020).
Rhodes, D., et al., "Zinc Fingers," Scientific American 268(2):56-65, Scientific American, United States (Feb. 1993).
Roon-Mom, W.M., et al., "Overview on Applications of Antisense-Mediated Exon Skipping," Methods in Molecular Biology 867:79-96, Springer, United States (2012).
Sa, J.K., et al., "Pharmacogenomic Analysis of Patient-Derived Tumor Cells In Gynecologic Cancers," Genome Biology 20(1):253, BioMed Central Ltd, United Kingdom (Nov. 2019).
Segal, D.J. and Barbas, C.F., "Custom DNA-Binding Proteins Come of Age: Polydactyl Zinc-Finger Proteins," Curr. Opin. Biotechnol. 12(6):632-637, Elsevier, Netherlands (Dec. 2001).
Serajuddin, A.T., et al., "Solid Dispersion of Poorly Water-Soluble Drugs: Early Promises, Subsequent Problems, and Recent Breakthroughs," J. Pharm. Sci. 88(10):1058-1066, Elsevier, Netherlands (Oct. 1999).
Seth, S., et al., "Delivery and Biodistribution of SiRNA for Cancer Therapy: Challenges and Future Prospects," Therapeutic Delivery 3(2):245-261, Future Science, United States (Feb. 2012).
Sharei A., et al., "A Vector-free Microfluidic Platform for Intracellular Delivery," Proceedings of the National Academy of Sciences 110(6):2082-2087, National Academy of Sciences, United States (Feb. 2013).
Shegokar, R., et al., "SiRNA Delivery: Challenges and Role of Carrier Systems, " Pharmazie 66(5):313-318, Govi-Verlag Pharmazautischer Verlag, Germany, (May 2011).
Sheldrick, G. M., "Crystal structure refinement with SHELXL," Acta. Crystallogr. C. Struct. Chem. 71(Pt 1):3-8, International Union of Crystallography, United Kingdom (Jan. 2015).
Sizemore, S. T., et al., "Synthetic Lethality of PARP Inhibition and Ionizing Radiation is p53-dependent," Mol. Cancer Res. 16(7):1092-1102, American Association for Cancer Research, United States (2018).
Sullivan, P., et al., "USP1 Inhibitors Show Robust Combination Activity and a Distinct Resistance Profile from PARP Inhibitors," Eur. J. Cancer 138(S2):S7-S8, Abstract ORAL003, 2 pages, Elsevier, Netherlands (Oct. 2020).
The United States Pharmacopeia—National Formulary, "941 X-ray Diffraction," 23(18):1843-1844, The United States Pharmacopeial Convention, United States (1995).
Thompson, L.A and Ellman, J.A., "Synthesis and Applications of Small Molecule Libraries," Chemical Review 96(1):555-600, American Chemical Society, United States (1996).
Tuerk, C and Gold, L., "Systematic Evolution of Ligands by Exponential Enrichment: RNA Ligands To Bacteriophage T4 Dna Polymerase," Science 249(4968):505-510, American Association for the Advancement of Science, United States (Aug. 1990).
Vader, P., et al., "Polymeric Carrier Systems for SiRNA Delivery," Current Topics in Medicinal Chemistry 12(2):108-119, Bentham Science, United Arab Emirates (2012).
Van Tonder, E.C., et al., "Preparation and Physicochemical Characterization of 5 Niclosamide Solvates and 1 Hemisolvate," AAPS PharmSciTech 5(1):E12, American Association of Pharmaceutical Scientists, United States (2004).
Varasteh, M., et al., "Quantitative determination of polymorphic impurity by X-ray powder diffractometry in an OROS formulation," Int. J. Pharm. 366(1-2):74-81, Elsevier, Netherlands (2009).
Wang, C., et al., "ATM-Deficient Colorectal Cancer Cells are Sensitive to the PARP Inhibitor Olaparib," Transl. Oncol. 10(2):190-196, Elsevier, Netherlands (Apr. 2017).
Yamamoto, T., et al., "Antisense Drug Discovery and Development," Future Med. Chem. 3(3):339-365, Future Science, United Kingdom (2011).
Zhang, Y., et al., "Comparison of Non-Canonical PAMs for CRISPR/Cas9-Mediated DNA Cleavage in Human Cells," Sci. Rep. 4:5405, Nature Publishing Group, United Kingdom (Jun. 2014).
Sanna, M., et al., "Water Solubility Enhancement of Pyrazolo[3,4-d]pyrimidine Derivatives via Miniaturized Polymer-Drug Microarrays," ACS Med Chem Lett 9(3):193-197, American Chemical Society, United States (Jan. 2018).
Sanna, M., et al., "Supplementary data: Water Solubility Enhancement of Pyrazolo[3,4-d]pyrimidine Derivatives via Miniaturized Polymer-Drug Microarrays," ACS Med Chem Lett pp. 1-12, American Chemical Society, United States (Mar. 2018), accessed at https://pubs.acs.org/doi/abs/10.1021/acsmedchemlett.7b00456, accessed on Jan. 3, 2024.

COMPOSITIONS OF SUBSTITUTED PYRAZOLOPYRIMIDINES AND USES THEREOF

BACKGROUND

Field of the Invention

The present disclosure relates to pharmaceutical formulations comprising substituted pyrazolopyrimidines. More particularly, this disclosure relates to bioavailable amorphous solid dispersions of substituted pyrazolopyrimidines. This disclosure also relates to processes for preparing these amorphous solid dispersions, pharmaceutical compositions comprising such dispersions, and to methods of use thereof.

Background of the Invention

Substituted pyrazolopyrimidines, such as 6-(4-cyclopropyl-6-methoxypyrimidin-5-yl)-1-(4-(1-isopropyl-4-(trifluoromethyl)-1H-imidazol-2-yl) benzyl)-1H-pyrazolo[3,4-d]pyrimidine of Formula (II) and 6-(4-cyclopropyl-6-methoxypyrimidin-5-yl)-1-(4-(5-methyl-3-(trifluoromethyl)-1H-pyrazol-1-yl) benzyl)-1H-pyrazolo[3,4-d]pyrimidine of Formula (III) are inhibitors of ubiquitin-specific-processing protease 1 (USP1). U.S. Provisional Patent Appl. No. 62/946,263 discloses compounds of Formula II and Formula III and is herein incorporated by reference in its entirety.

It has now been determined that these compounds have limited solubility in aqueous environments at physiological pH and less than optimal bioavailability. Therefore, a need exists for bioavailable formulations of substituted pyrazolopyrimidines compounds which exhibit improved solubility and bioavailability, have a desirable pharmaceutical profile, and are amenable to manufacturing conditions.

SUMMARY OF THE DISCLOSURE

Accordingly, the present disclosure provides an amorphous solid dispersion, comprising:

a compound of Formula I:

(I)

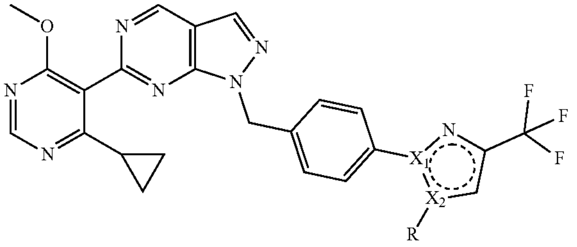

or a pharmaceutically acceptable salt thereof, wherein:

R is $C_{1-3}$ alkyl; and $X_1$ and $X_2$ are independently selected from the group consisting of N and C; and a polymer; wherein said compound is in a solid substantially amorphous form and is dispersed in the polymer.

In one aspect, the compound is 6-(4-cyclopropyl-6-methoxypyrimidin-5-yl)-1-(4-(1-isopropyl-4-(trifluoromethyl)-1H-imidazol-2-yl) benzyl)-1H-pyrazolo[3,4-d]pyrimidine of Formula II:

(II)

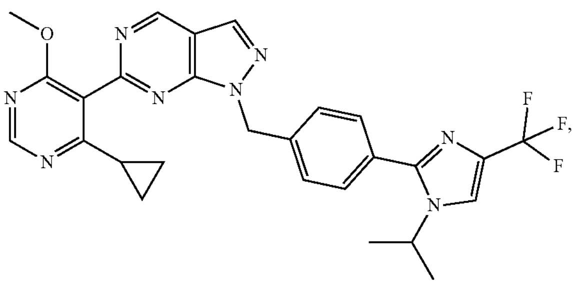

or a pharmaceutically acceptable salt, thereof.

In another aspect, the compound is 6-(4-cyclopropyl-6-methoxypyrimidin-5-yl)-1-(4-(5-methyl-3-(trifluoromethyl)-1H-pyrazol-1-yl) benzyl)-1H-pyrazolo[3,4-d]pyrimidine of Formula (III):

(III)

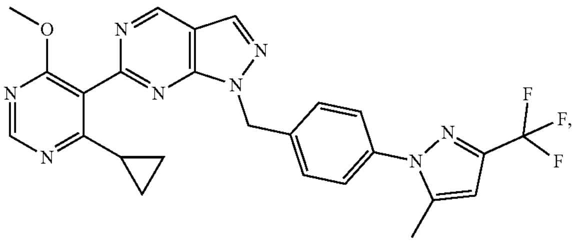

or a pharmaceutically acceptable salt, thereof.

Another aspect of the present invention provides a method of making the amorphous solid dispersions.

Another aspect of the present invention provides an oral dosage form comprising the amorphous solid dispersions disclosed herein.

In a further aspect, the present invention relates to methods of treating cancer by administering one of said solid amorphous dispersion, pharmaceutical composition or dosage form to a patient in need thereof.

The foregoing and other objectives, features, and advantages of the invention will be more readily understood upon consideration of the following detailed description of the invention, taken in conjunction with the accompanying drawings.

BRIEF DESCRIPTION OF DRAWINGS

FIG. 5 shows a modulated differential scanning calorimetry (mDSC) trace of ASD of Formula II with 33% drug loading dispersed in HPMC-AS.

FIG. 6 shows an XRPD pattern of ASD of Formula II with 33% drug loading dispersed in HPMC-AS.

FIG. 7 shows a PLM image of ASD sample of Formula II with 33% drug loading dispersed in HPMC-AS.

FIG. 11 (*a*) shows PLM image of ASD of Formula III dispersed in Eudragit L100-55 with 20% drug loading; 11(*b*) shows PLM image of ASD of Formula III dispersed in Eudragit L100-55 with 33% drug loading; 11(*c*) shows PLM image of ASD of Formula III dispersed in Eudragit L100-55 with 50% drug loading; 11(*d*) shows PLM image of ASD of Formula III dispersed in HPMCAS-HG with 20% drug loading.

FIG. 14 shows mDSC of ASD of Formula III with 33% drug loading dispersed in HPMC-AS.

DETAILED DESCRIPTION

Figure 1:
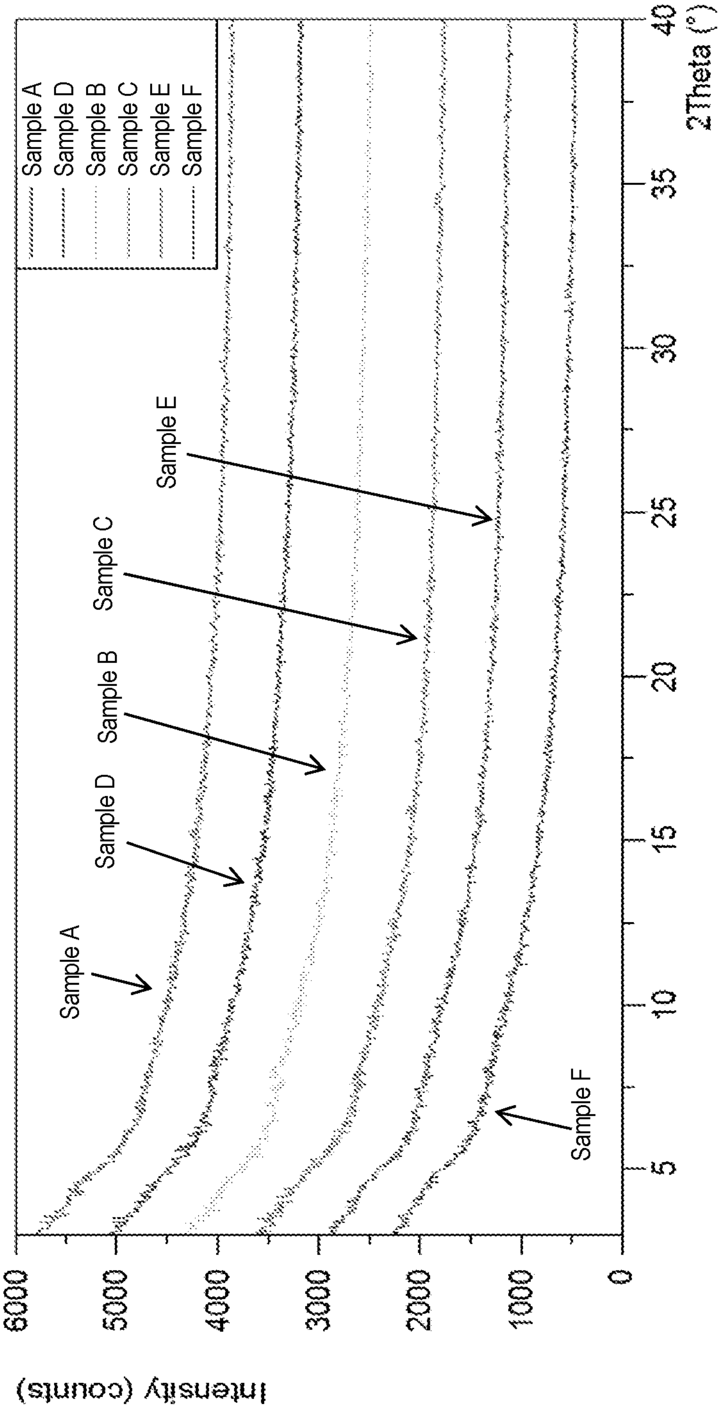
FIG. 1 shows an X-ray powder diffraction (XRPD) overlay of six amorphous solid dispersions (ASD) of compound of Formula II.
Figure 2A:
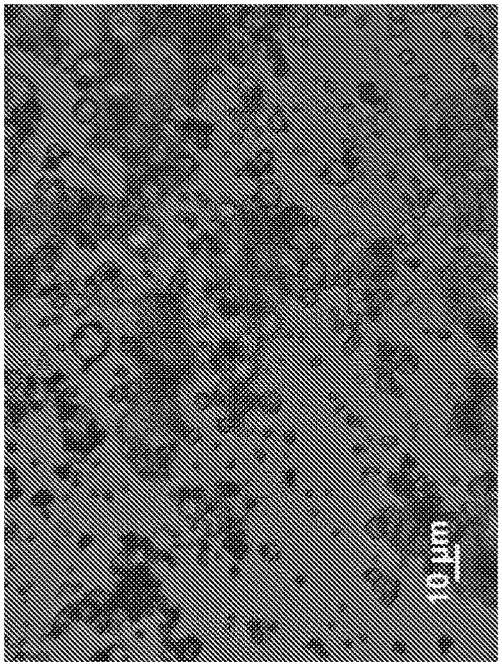
FIG. 2(*a*) shows PLM image of ASD of compound of Formula II dispersed in Eudragit L100-55 with 20% drug loading; 2(*b*) shows PLM image of ASD of compound of Formula II dispersed in Eudragit L100-55 with 33% drug loading; 2(*c*) shows PLM image of ASD of compound of Formula II dispersed in Eudragit L100-55 with 50% drug loading; 2(*d*) shows PLM image of ASD of compound of Formula II dispersed in HPMCAS-HG with 20% drug loading.
Figure 2B:
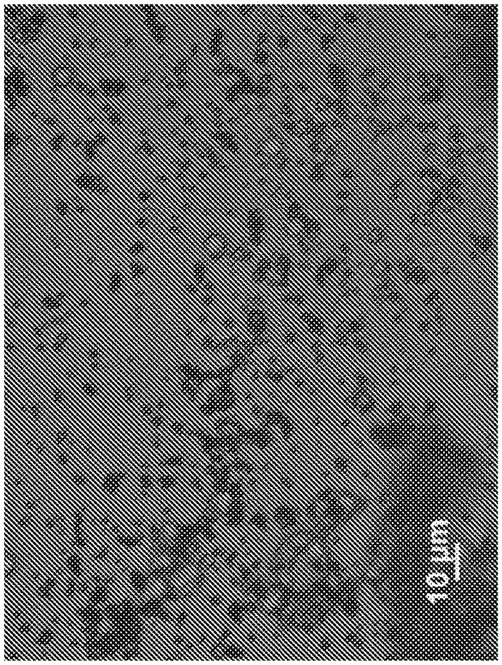
Figure 2C:
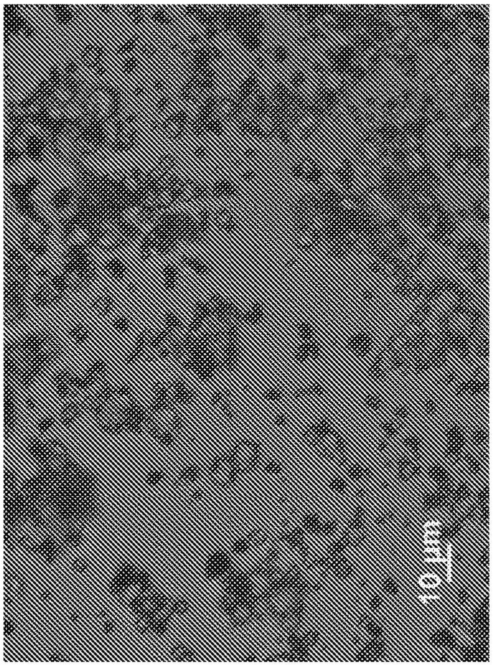
Figure 2D:
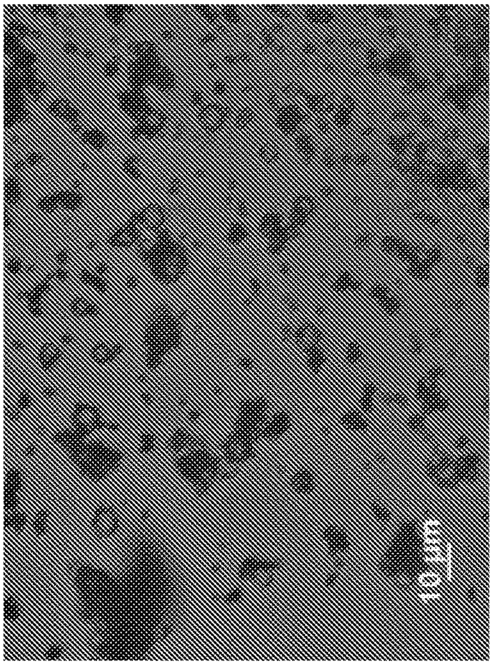
Figure 3:
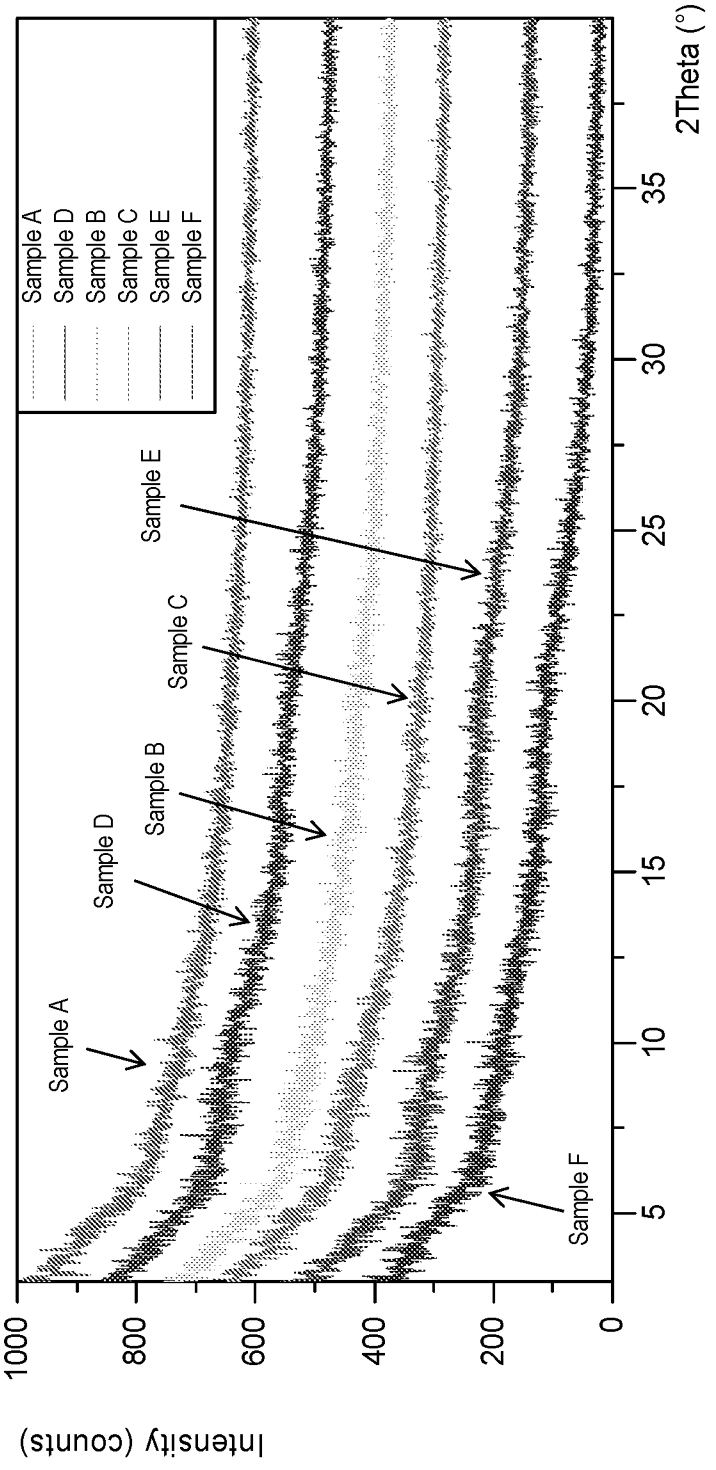
FIG. 3 shows an XRPD overlay of ASDs of Formula II after 12 days at 40° C./75% RH chamber.

Pyrazolopyrimidine compounds of Formulae I, II and III are poorly soluble in water at physiological pHs (from pH 1.5-8.0). Studies of these compounds indicate that these compounds are BCS class II compounds (low solubility/high permeability). Consequently, these compounds have low bioavailability. Poor bioavailability is also often accompanied by highly variable patient blood levels and unpredictable dose/therapeutic effects due to erratic absorption of the drug by the patient. Accordingly, a need exists for compositions and methods to increase the solubility of these compounds.

A reduction in particle size improves the dissolution rate significantly, which provides better absorption potential and potentially leads to improved therapeutics. Wet milling and nanotechnology to prepare nanosuspensions is one approach that can be applied to enhance solubility of poorly water-soluble drugs. Nanosuspensions are submicron colloidal dispersions of nanosized drug particles stabilized by surfactants and have been evaluated in Examples 8, 9 and 10 herein. Although nanosuspensions, as described herein, enhance dissolution rate of drug, there are practical limitations as the desired bioavailability enhancement may not always be achieved simply by particle size reduction.

In recent years, solid dispersions have attracted attention in the field of oral preparations, especially as one mechanism for formulating poorly soluble compounds. However, to use this technology effectively, identification of an appropriate carrier that is compatible with the drug is necessary. The solid dispersions prepared from different methods may differ in properties, such as porosity, surface area, density, stability, hygroscopicity, dissolution and consequently, bioavailability.

Amorphous solid dispersions are high energy formulations that may present additional challenges since they are, by nature, thermodynamically unstable. Consequently, their successful development depends in good measure on the understanding of the specific interactions responsible for their stabilization (Serajuddin, A. T. M. J. Pharm. Sci. 1999, 88, 1058-1066; Janssens, S. and Van den Mooter, G. J. Pharm. Phamacol. 2009, 61, 1571-1586).

Amorphous solid dispersions described herein show a significant enhancement in oral bioavailability and/or an improvement in dose linearity at higher doses.

In one aspect, the present invention provides an amorphous solid dispersion, comprising a compound of Formula I:

(I)

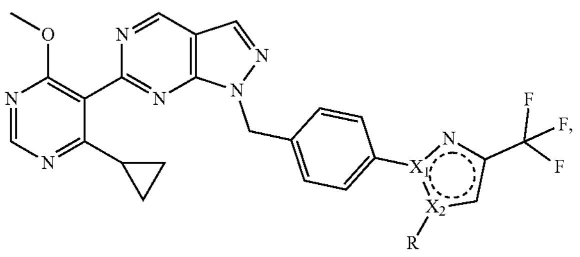

or a pharmaceutically acceptable salt thereof, wherein R is $C_{1-3}$ alkyl; and $X_1$ and $X_2$ are independently selected from the group consisting of N and C, wherein said compound is in a substantially amorphous form and is dispersed in a polymer.

In another aspect, the compound is 6-(4-cyclopropyl-6-methoxypyrimidin-5-yl)-1-(4-(1-isopropyl-4-(trifluoromethyl)-1H-imidazol-2-yl)benzyl)-1H-pyrazolo[3,4-d]pyrimidine of Formula II:

(II)

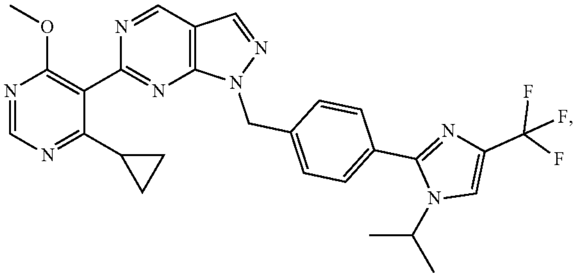

or a pharmaceutically acceptable salt, thereof.

In another aspect, the compound is 6-(4-cyclopropyl-6-methoxypyrimidin-5-yl)-1-(4-(5-methyl-3-(trifluoromethyl)-1H-pyrazol-1-yl)benzyl)-1H-pyrazolo[3,4-d]pyrimidine of Formula (III):

(III)

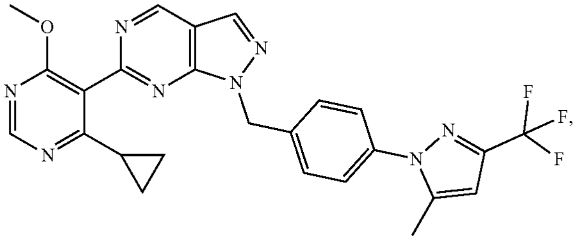

or a pharmaceutically acceptable salt, thereof.

In an aspect, the starting material of the solid dispersions can be crystalline forms, amorphous form, salts, or solvates thereof of a compound of Formula II.

In an aspect, the starting material of the solid dispersions is a crystalline form of a compound of Formula II.

In another aspect, the starting material of the solid dispersions can be crystalline forms, amorphous form, salts, or solvates thereof of a compound of Formula III.

In an aspect, the starting material of the solid dispersions is a crystalline form of a compound of Formula III.

The polymer used in amorphous dispersion is found to play a role in stabilizing amorphous solid dispersions. In an aspect, suitable polymers include those that reduce or prevent the conversion of amorphous compounds of this invention to a crystalline form.

In an aspect, suitable polymers include ionic cellulosic polymers which include, without limitation, carboxymethylcellulose (CMC) and its sodium or calcium salts; carboxyethyl cellulose (CEC); carboxymethyl ethylcellulose (CMEC); hydroxyethylmethyl cellulose acetate phthalate; hydroxyethyl methylcellulose acetate succinate; hydroxypropyl methylcellulose phthalate (HPMCP); hydroxypropyl methylcellulose succinate; hydroxypropyl cellulose acetate phthalate (HPCAP); hydroxypropyl cellulose acetate succinate (HPCAS); hydroxypropyl methylcellulose acetate phthalate (HPMCAP); hydroxypropyl methylcellulose acetate succinate (HPMCAS); hydroxypropyl methylcellulose acetate trimellitate (HPMCAT); hydroxypropyl cellulose butyrate phthalate; carboxymethyl ethylcellulose and its sodium salt; cellulose acetate phthalate (CAP); methylcellulose acetate phthalate; cellulose acetate trimellitate (CAT); cellulose acetate terephthalate; cellulose acetate isophthalate; cellulose propionate phthalate; cellulose propionate trimellitate; cellulose butyrate trimellitate; and mixtures thereof.

In an aspect, suitable polymers include nonionic cellulosic polymers which include, without limitation, methylcellulose (MC); ethyl cellulose (EC); hydroxyethyl cellulose (HEC); hydroxypropyl cellulose (HPC); hydroxypropyl methylcellulose (HPMC); hydroxypropyl methylcellulose acetate; hydroxyethyl methylcellulose; hydroxyethyl cellulose acetate; hydroxyethyl ethylcellulose; and mixtures thereof.

In an aspect, suitable polymers include methacrylic acid copolymers and aminoalkyl methacrylate copolymers, which are available, for example, under the trade names EUDRAGIT® L, S, NE, RL, RS, and E. Other exemplary polymers include carboxylic acid functionalized polymethacrylates and amine-functionalized polymethacrylates; poly (vinyl acetal) diethylaminoacetate; polyvinyl alcohol (PVA); and polyvinyl alcohol/polyvinyl acetate (PVA/PVAc) copolymers; and mixtures thereof.

In another aspect, suitable polymers include homopolymers of N-polyvinyl pyrrolidone (NVP), including, for example, water-soluble polyvinylpyrrolidones (PVPs or povidones), such as KOLLIDON® 12 PF, 17 PF, 25, 30, and 90 F; water-soluble copolymers of PVP and vinylacetate (VA), such as KOLLIDON® VA64; and water-insoluble cross-linked polyvinylpyrrolidones (crospovidone), such as KOLLIDON® CL, CL-M, and SR, which are available from BASF; and mixtures thereof.

In another aspect, suitable polymers include polymeric ethers and esters of polyhydric alcohols, polyethylene glycol (PEG) and polypropylene glycol (PPG) homopolymers and copolymers (PEG/PPG); polyethylene/polyvinyl alcohol (PE/PVA) copolymers; dextrin; pullulan; acacia; tragacanth; sodium alginate; propylene glycol alginate; agar powder; gelatin; starch; processed starch; glucomannan; chitosan; and mixtures thereof. Other exemplary polymeric ethers include polyethylene oxides, polypropylene oxides, and polyoxyethylene-polyoxypropylene block copolymers (poloxamers) such as those available from BASF under the trade names LUTROL® F 68, F 127, and F 127-M; and mixtures thereof.

In a particular aspect, the polymer is hydroxypropyl methylcellulose acetate succinate (HPMCAS).

In a particular aspect, the polymer is poly (methacylic acid)-co-methyl methacrylate (EUDRAGIT L-100® or EUDRAGIT L100-55®)).

In an aspect, the amorphous solid dispersion comprises a compound of Formula II dispersed in hydroxypropyl methylcellulose acetate succinate.

In an aspect, the amorphous solid dispersion comprises a compound of Formula II dispersed in poly (methacylic acid)-co-methyl methacrylate.

In an aspect, the amorphous solid dispersion comprises a compound of Formula III dispersed in hydroxypropyl methylcellulose acetate succinate.

In an aspect, the amorphous solid dispersion comprises a compound of Formula III dispersed in poly (methacylic acid)-co-methyl methacrylate In an aspect, the polymer generally comprises about 40% to about 95% of the resulting solid dispersion, often of the solid dispersion, and more typically, about 50% to about 70% of the solid dispersion, based on weight.

The drug loading in solid amorphous dispersions has been found to be important. Above a certain drug loading, there is a high probability in re-crystallization of amorphous solid dispersion during shelf life and this diminishes the benefit of the improved solubility and bioavailability.

In an aspect, the amorphous solid dispersions comprise from about 1% to about 50% w/w of compound of Formula II.

In further aspects, the amorphous solid dispersions comprise about 20% w/w or about 33% w/w or about 50% w/w of compound of Formula II.

In an aspect, the amorphous solid dispersions comprise about 1% to about 50% w/w of compound of Formula III.

In further aspects, the amorphous solid dispersions comprise about 20% w/w or about 33% w/w or about 50% w/w of compound of Formula III.

In a further aspect, pharmaceutical compositions comprising solid dispersions of compounds of Formula II as disclosed by present invention comprise less than about 20% crystalline compound of Formula II, less than about 15% crystalline compound of Formula II, less than about 10% crystalline compound of Formula II, less than about 8% crystalline compound of Formula II, less than about 5% crystalline compound of Formula II, less than about 2% crystalline compound of Formula II, less than about 1% crystalline compound of Formula II, or less than about 0.5% crystalline compound of Formula II. In an aspect, pharmaceutical compositions of the invention are substantially free of crystalline compound of Formula II as determined by XRPD.

In a further aspect, pharmaceutical compositions comprising solid dispersions of compounds of Formula III as disclosed by present invention comprise less than about 20% crystalline compound of Formula III, less than about 15% crystalline compound of Formula III, less than about 10% crystalline compound of Formula III, less than about 8% crystalline compound of Formula III, less than about 5% crystalline compound of Formula III, less than about 2% crystalline compound of Formula III, less than about 1% crystalline compound of Formula III, or less than about 0.5% crystalline compound of Formula III. In an aspect, pharmaceutical compositions of the invention are substantially free of crystalline compound of Formula III as determined by XRPD.

The term "solid dispersion" means a system in a solid state comprising at least two components, wherein one component is dispersed throughout the other component.

The term "amorphous" refers to a state in which the material lacks long-range order at the molecular level and, depending upon temperature, may exhibit the physical properties of a solid or a liquid. Typically, such materials do not give distinctive X-ray diffraction patterns.

The term "crystalline" refers to a solid phase in which the material has a regular ordered internal structure at the molecular level and gives a distinctive X-ray diffraction pattern with defined peaks.

The term "substantially amorphous" as used herein is intended to mean that greater than 50%; or greater than 55%; or greater than 60%; or greater than 65%; or greater than 70%; or greater than 75%; or greater than 80%; or greater than 85%; or greater than 90%; or greater than 95%, or greater than 99% of the compound present in a composition is in amorphous form.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The terms "treat" or "treatment" refer to therapeutic, prophylactic, palliative or preventative measures. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

The term "therapeutically effective amount." as used herein, refers to an amount of the drug Substance present in the amorphous dispersion or pharmaceutical composition being administered that is sufficient to prevent development of or alleviate to some extent one or more of the symptoms of the disease being treated. Likewise, a therapeutically effective amount of a pharmaceutical composition refers to an amount of such composition that is Sufficient to prevent development of, or alleviate to some extent, one or more of the symptoms of the disease being treated.

In an aspect, solid dispersions of the present invention can be prepared by melt-extrusion, spray-drying, lyophilization, and solution-evaporation.

Melt-extrusion is the process of embedding a compound in a thermoplastic carrier. The mixture is processed at elevated temperatures and pressures, which disperses the compound in the matrix at a molecular level to form a solid solution. Extruded material can be further processed into a variety of dosage forms, including capsules, tablets and transmucosal systems.

For spray dried solid dispersions, the solid dispersion can be made by a) mixing the compound and polymer in a solvent to provide a feeder Solution; and b) spray drying the feeder solution to provide the solid dispersion.

For the lyophilization technique, the compound and carrier can be co-dissolved in a common solvent, frozen and sublimed to obtain a lyophilized molecular dispersion.

For the solution-evaporation method, the solid dispersion can be prepared by dissolving the compound in a suitable liquid solvent and then incorporating the solution directly into the melt of a polymer, which is then evaporated until a clear, solvent free film is left, the film is further dried to constant weight.

In a particular aspect, solid dispersions of the present invention are prepared by spray drying.

Solvents suitable for spray-drying can be any organic compound with relatively low toxicity in which the drug and polymer are mutually soluble.

In an aspect, suitable solvents include alcohols such as methanol, ethanol, n-propanol, iso-propanol, butanol, ketones such as acetone, methyl ethyl ketone and methyl iso-butyl ketone; esters such as ethyl acetate and propylacetate; and various other solvents such as acetonitrile, methylene chloride, toluene, 1,1,1-trichloroethane, dimethyl acetamide, dimethylsulfoxide and mixtures thereof.

In a further aspect, mixtures of solvents, such as 50% methanol and 50% acetone, can also be used, as can mixtures with water, so long as the polymer and drug are sufficiently soluble to make the spray-drying process practicable.

In an aspect, the amorphous solid dispersions as disclosed herein were subjected to accelerated stability studies by exposing the formulations to stress conditions 25° C., 30%

RH; 25° C., 75% RH; 40° C., 75% RH. The samples were analyzed for the presence of crystallinity, at different time points (5 days and 12 days).

In an aspect, the solid dispersions of compound of Formula II as described herein, exhibit stability against recrystallization when exposed to humidity and temperature over time. In a further aspect, solid dispersions of compound of Formula II dispersed in HPMC-AS exhibited superior stability when exposed to humidity and temperature over time.

In a further aspect, the solid dispersions of compound of Formula III as described herein, exhibit stability against recrystallization when exposed to humidity and temperature over time. In a further aspect, solid dispersions of compound of Formula III dispersed in HPMC-AS exhibited superior stability when exposed to humidity and temperature over time. In an aspect, physical stability of the dispersions was determined using DSC and XRPD.

The amorphous solid dispersion of the present invention may be used in a wide variety of dosage forms for administration by a wide variety of routes, including, but not limited to, oral, nasal, rectal, vaginal, transdermal, buccal, subcutaneous, intravenous, and pulmonary.

In certain aspects, the amorphous solid dispersion as disclosed herein is formulated as an oral dosage form. Exemplary oral dosage forms include powders or granules that can be taken orally either dry or reconstituted by addition of water to form a paste, slurry, suspension or solution, tablets, capsules, or pills. Various additives can be mixed, ground or granulated with the solid dispersion as described herein to form a material suitable for the above dosage forms. Potentially beneficial additives may fall generally into the following classes: other matrix materials or diluents, Surface active agents, fillers, disintegrants, binders, lubricants, and pH modifiers (e.g., acids, bases, or buffers). Examples of other matrix materials, fillers, or diluents include lactose, mannitol, xylitol, micro crystalline cellulose, calcium diphosphate, and starch. Examples of surface active agents include sodium lauryl sulfate and polysorbate 80.

In an aspect, the oral dosage form of the present invention is a suspension.

In an aspect, pharmaceutical formulations comprising substituted pyrazolopyrimidines as disclosed herein can be used to inhibit the activity of a USP1 protein. For example, in some aspects, a method of inhibiting a USP1 protein comprises contacting the USP1 protein with a pharmaceutical formulations as disclosed herein. The contacting can occur in vitro or in vivo.

In an aspect, pharmaceutical formulations comprising substituted pyrazolopyrimidines as disclosed herein can be used to treat a "USP1 protein mediated disorder." A USP1 protein mediated disorder is any pathological condition in which a USP1 protein is known to play a role. In some aspects, a USP1 protein mediated disorder is a proliferative disease such as cancer.

Various methods of treating diseases and disorders with pharmaceutical formulations comprising substituted pyrazolopyrimidines are provided herein. Exemplary diseases and disorders that may be treated with the pharmaceutical formulations comprising substituted pyrazolopyrimidines include, but are not limited to, cancer.

In some aspects, methods of treating cancer with pharmaceutical formulations comprising substituted pyrazolopyrimidines are provided. Such methods comprise administering to a subject with cancer a therapeutically effective amount of pharmaceutical formulation as disclosed herein.

In some aspects, the cancer to be treated with pharmaceutical formulations comprising substituted pyrazolopyrimidines as disclosed herein is selected from a hematological cancer, a lymphatic cancer, and a DNA damage repair pathway deficient cancer. In some aspects, the cancer to be treated with a pharmaceutical formulations comprising substituted pyrazolopyrimidines as disclosed herein is a cancer that comprises cancer cells with a mutation in a gene encoding p53. In some aspects, the cancer to be treated with pharmaceutical formulations comprising substituted pyrazolopyrimidines as disclosed herein is a cancer that comprises cancer cells with a loss of function mutation in a gene encoding p53. In some aspects, the cancer to be treated with pharmaceutical formulations comprising substituted pyrazolopyrimidines as disclosed herein is a cancer that comprises cancer cells with a mutation in a gene encoding BRCA1. In some aspects, the cancer to be treated with pharmaceutical formulations comprising substituted pyrazolopyrimidines as disclosed herein is a cancer that comprises cancer cells with a mutation in a gene encoding BRCA2. In some aspects, the cancer to be treated with pharmaceutical formulations comprising substituted pyrazolopyrimidines as disclosed herein is a cancer that comprises cancer cells with a loss of function mutation in a gene encoding ATM.

In some aspects, the cancer to be treated with pharmaceutical formulations comprising substituted pyrazolopyrimidines as disclosed herein is selected from non-small cell lung cancer (NSCLC), osteosarcoma, ovarian cancer, and breast cancer. In some aspects, the cancer is ovarian cancer or breast cancer. In some aspects, the cancer is ovarian cancer. In some aspects, the cancer is breast cancer. In some aspects, the cancer is a triple negative breast cancer.

In some aspects, the cancer to be treated with pharmaceutical formulations comprising substituted pyrazolopyrimidines as disclosed herein is selected from the group consisting of bone cancer, including osteosarcoma and chondrosarcoma; brain cancer, including glioma, glioblastoma, astrocytoma, medulloblastoma, and meningioma; soft tissue cancer, including rhabdoid and sarcoma; kidney cancer; bladder cancer; skin cancer, including melanoma; and lung cancer, including non-small cell lung cancer; colon cancer, uterine cancer; nervous system cancer; head and neck cancer; pancreatic cancer; and cervical cancer.

Various methods of treating cancer with pharmaceutical formulations comprising substituted pyrazolopyrimidines are provided herein. In some aspects, a therapeutically effective amount of pharmaceutical formulation as disclosed herein is administered to a subject with cancer, wherein the cancer comprises cancer cells with elevated levels of RAD18. In some aspects, the elevated levels of RAD18 are elevated RAD18 protein levels. In some aspects, the elevated levels of RAD18 are elevated RAD18 mRNA levels. In some aspects, elevated levels of RAD18 (e.g., RAD18 protein and/or RAD18 mRNA) have been detected (e.g., in a cancer sample obtained from the subject) prior to the administration. That is, in some aspects, a subject's cancer has been tested for RAD18 protein or mRNA prior to beginning treatment with a USP1 inhibitor.

In some aspects, such methods comprise (a) identifying a cancer in a subject as a USP1 inhibitor-sensitive cancer and then (b) administering a therapeutically effective amount of a pharmaceutical formulation as disclosed herein to the subject.

In some aspects, such methods comprise (a) detecting levels of RAD18 (e.g., RAD18 protein and/or RAD18 mRNA) in cancer cells (e.g., in a cancer sample obtained from the subject) and then (b) administering a therapeutically effective amount of a pharmaceutical formulation as disclosed herein to a subject having a cancer comprising cells with elevated levels of RAD18.

In some aspects, such methods comprise administering to a subject with triple negative breast cancer a therapeutically effective amount of a pharmaceutical formulation as disclosed herein.

In some aspects, pharmaceutical formulations comprising substituted pyrazolopyrimidines as disclosed herein is used to treat a cancer, wherein the cancer is a homologous-recombination deficient cancer. In some aspects, pharmaceutical formulations comprising substituted pyrazolopyrimidines as disclosed herein is used to treat a cancer, wherein the cancer comprises cancer cells with a mutation in a gene encoding p53. In some aspects, pharmaceutical formulations comprising substituted pyrazolopyrimidines as disclosed herein is used to treat a cancer, wherein the cancer comprises cancer cells with a loss of function mutation in a gene encoding p53. In some aspects, pharmaceutical formulations comprising substituted pyrazolopyrimidines as disclosed herein is used to treat a cancer that does not have a defect in the homologous recombination pathway.

In some aspects, pharmaceutical formulations comprising substituted pyrazolopyrimidines as disclosed herein is used to treat a cancer, wherein the cancer is a BRCA1 mutant cancer. In some aspects, pharmaceutical formulations comprising substituted pyrazolopyrimidines as disclosed herein is used to treat a cancer, wherein the cancer is a BRCA2 mutant cancer. In some aspects pharmaceutical formulations comprising substituted pyrazolopyrimidines as disclosed herein is used to treat a cancer, wherein the cancer is a BRCA1 mutant cancer and a BRCA2 mutant cancer. In some aspects, the cancer is not a BRCA1 mutant cancer or a BRCA2 mutant cancer. In some aspects, the cancer is a BRCA1 deficient cancer. In some aspects, the cancer is a BRCA2 deficient cancer. In some aspects, the cancer is a BRCA1 deficient cancer and a BRCA2 mutant cancer.

In some aspects, pharmaceutical formulations comprising substituted pyrazolopyrimidines as disclosed herein is used to treat a cancer, wherein the cancer is an ATM mutant cancer. In some aspects, the cancer is not an ATM mutant cancer. In some aspects, the cancer is an ATM deficient cancer.

In some aspects, pharmaceutical formulations comprising substituted pyrazolopyrimidines as disclosed herein is used to treat a cancer, wherein the cancer is a PARP inhibitor resistant or refractory cancer. In some aspects, pharmaceutical formulations comprising substituted pyrazolopyrimidines as disclosed herein is used to treat a cancer, wherein the cancer is a PARP inhibitor resistant or refractory BRCA1-deficient cancer.

In an aspect, the cancer is a BRCA1 and/or BRCA2 mutant cancer, wherein the cancer comprises cells with elevated levels of RAD18, e.g., wherein the elevated levels of RAD18 are at least as high as the RAD18 protein and/or mRNA levels in ES2 cells or wherein the elevated levels of RAD18 are higher than the RAD18 protein and/or mRNA levels in HEP3B217 cells. In some aspects, a triple negative breast cancer is a BRCA1 and/or BRCA2 mutant cancer.

In some instances, the cancer is a solid cancer. In some instances, the cancer is a hematological/lymphatic cancer. In some instances, the cancer is a DNA damage repair pathway deficient cancer. In some instances, the cancer is a homologous-recombination deficient cancer. In some instances, the cancer comprises cancer cells with a mutation in a gene encoding p53. In some instances, the cancer comprises cancer cells with a loss of function mutation in a gene encoding p53. In some instances, the cancer is selected from the group consisting of non-small cell lung cancer (NSCLC), osteosarcoma, ovarian cancer, and breast cancer (including triple negative breast cancer). In some instances, the cancer is ovarian cancer or breast cancer (including triple negative breast cancer). In some instances, the cancer is ovarian cancer. In some instances, the cancer is breast cancer (including triple negative breast cancer.)

In some aspects, pharmaceutical formulations comprising substituted pyrazolopyrimidines as disclosed herein is used in combination with one or more additional therapeutic agents to treat cancer. It has been reported that p53 status determines PARP inhibitor sensitization (Sa et al. Genome Biology, (2019) 20:253) and that BRCA1/2 status predicts the efficacy of PARP inhibitors in the clinic (Audeh et al. Lancet (2010) 376 (9737), 245-51). As shown below, p53 mutant cancers and BRCA mutant cancers have increased sensitivity to USP1 inhibitors. Accordingly, in some aspects, pharmaceutical formulations comprising substituted pyrazolopyrimidines as disclosed herein is used in combination with a PARP inhibitor to treat cancer.

In some aspects, provided herein are pharmaceutical formulations comprising substituted pyrazolopyrimidines for use as a medicament or for use in preparing a medicament, e.g., for the treatment of cancer.

EXAMPLES

Example 1

General Methods of ASD Instrumental Measurements

X-Ray Powder Diffraction (XRPD)

XRPD was performed with a Panalytical X'Pert[3] Powder XRPD on a Si zero-background holder. The 2θ position was calibrated against a Panalytical Si reference standard disc. The parameters used are listed in Table 1.

TABLE 1

XRPD parameters

| Parameters | Reflection Mode |
|---|---|
| X-Ray wavelength | Cu, kα<br>Kα1 (Å): 1.540598,<br>Kα2 (Å): 1.544426,<br>Kα2/Kα1 intensity ratio: 0.50 |
| X-Ray tube setting | 45 kV, 40 mA |
| Divergence slit | Fixed 1/8° |
| Scan mode | Continuous |
| Scan range (°2θ) | 3-40 |
| Scan step time [s] | 18.87 |
| Step size (°2θ) | 0.0131 |
| Test Time | 4 min 15 s |

Polarized Light Microscopy (PLM)

PLM pictures were captured on Nikon DS-Fi2 upright microscope at room temperature.

Thermogravimetric Analysis (TGA) and Differential Scanning calorimetry (DSC)

TGA data was collected using a TA Discovery 550 TGA from TA Instruments. DSC was performed using a TA Q2000 DSC from TA Instruments. DSC was calibrated with Indium reference standard and the TGA was calibrated using nickel reference standard. Detailed parameters used are listed in Table 2.

TABLE 2

| TGA and DSC Parameters | | |
|---|---|---|
| Parameters | TGA | DSC |
| Method | Ramp | Ramp |
| Ramp Rate | — | 3° C./min |
| Sample pan | Aluminum, open | Aluminum, crimped |
| Temperature | RT~350° C. | RT~200° C. |
| Heating rate | 10° C./min | — |
| Purge gas | $N_2$ | $N_2$ |
| Modulation | — | 60 s |
| Amplitude | — | ±1° C. |

High Performance Liquid Chromatography (HPLC)

An Agilent 1100 HPLC was utilized, with detailed chromatographic conditions listed in Table 3.

TABLE 3

| Chromatographic conditions and parameters | | |
|---|---|---|
| Parameters | Agilent 1260 with DAD detector | |
| Column | XSelect CSH ™, C18, 3.5 μm, 4.6 by 150 mm, PN 186005270 | |
| Mobile phase | A: 0.05% formic acid in 95:5 $H_2O$:ACN<br>B: 0.05% formic acid in ACN | |
| Elution ratio | Time (min) | % B |
| | 15 | 52 |
| Run time | 11.0 min | |
| Flow rate | 1.0 mL/min | |
| Injection volume | 5 μL | |
| Detector | UV at 220 nm | |
| Column temperature | 30° C. | |
| Sampler temperature | RT | |
| Diluent | ACN | |

Example 2

Formulation Development for the Compound of Formula II (I) Preparation of ASDs of Formula II ASDs of 20%, 33%, and 50% API in excipients (HPMCAS-HG, Eudragit L100-55) were prepared by spray drying. About 0.4-0.8 g API material and corresponding excipient were weighed into a glass vial followed by addition of about 80 mL acetone/water (4:6, v/v) to dissolve the solids (acetone used first, then added water). The inlet temperature for spray drying was set as 150° C. and the outlet temperature was measured around 70° C. The ASDs were characterized by XRPD (FIG. 1) and PLM. The results are summarized in Table 4. PLM images displayed in FIG. 2*a* to FIG. 2*d* show that all ASD samples were fine particles without birefringence.

TABLE 4

| Characterization summary of ASD samples of Formula II | | | | |
|---|---|---|---|---|
| Sample ID | Excipient | Yield (%) | Amorphous? | Yield (%) |
| A | Eudragit L100-55 | 20 | Y | 28 |
| B | Eudragit L100-55 | 33 | Y | 70 |
| C | Eudragit L100-55 | 50 | Y | 47 |
| D | HPMC-AS HG | 20 | Y | 57 |
| E | HPMC-AS HG | 33 | Y | 49 |

TABLE 4-continued

| Characterization summary of ASD samples of Formula II | | | | |
|---|---|---|---|---|
| Sample ID | Excipient | Yield (%) | Amorphous? | Yield (%) |
| F | HPMC-AS HG | 50 | Y | 30 |

(II) Evaluation of ASDs of Formula II Under Stressed Conditions

Figure 8:
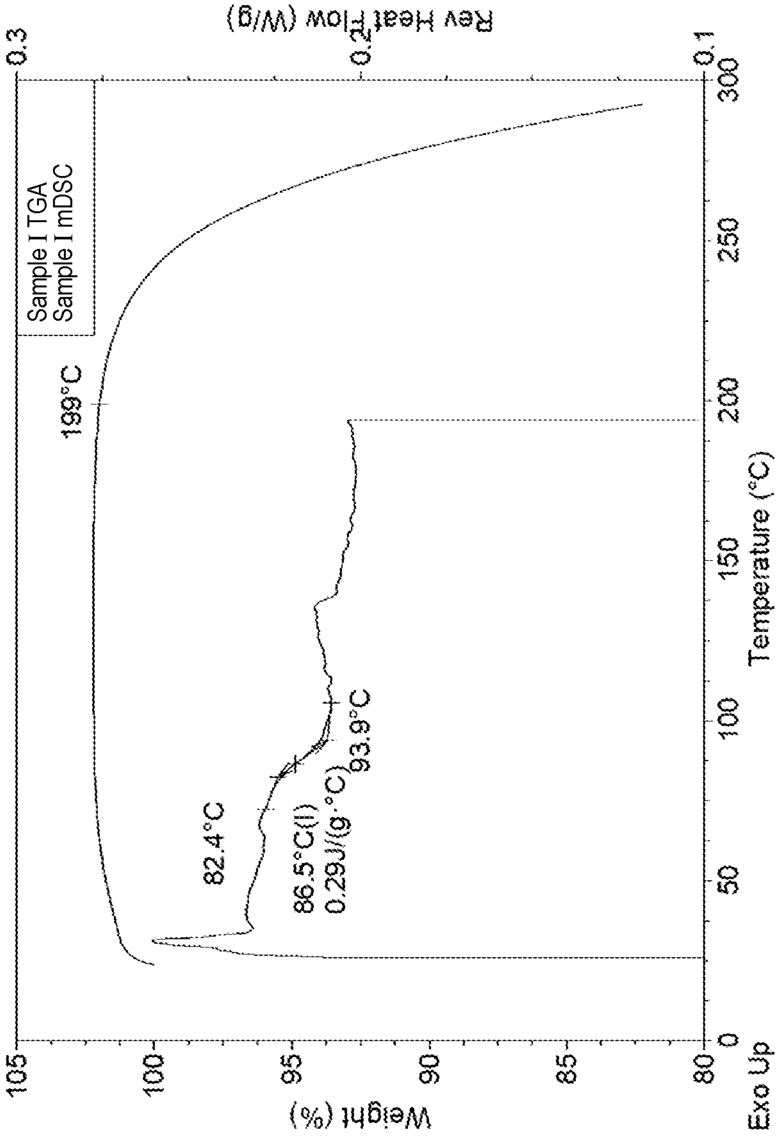
FIG. 8 shows Thermogravimetric analysis (TGA)/mDSC curves of ASD sample of Formula II with 33% drug loading dispersed in HPMCAS-HG.

The stability of the six ASDs were evaluated under stressed conditions (25° C./30% RH, 25° C./75% RH, 40° C./75% RH) over 5 and 12 days (Table 5 and Table 6, respectively). HPMCAS-HG ASDs exhibited better stability over 5 days, as no crystalline material was observed. Eudragit ASDs showed two incidents of the appearance of crystalline material. However, when the ASDs were exposed to stressed conditions over 12 days, the samples did not exhibit crystallinity. This is evidenced by the XRPD pattern overlay of the six ASDs under stressed conditions at 40° C./75% RH over 12 days as shown in FIG. 8.

TABLE 5

| Summary of ASDs samples of Formula II at under stressed conditions over five days | | | | | |
|---|---|---|---|---|---|
| ASD ID | Polymer used | Drug loading | 25° C., 30% RH | 25° C., 75% RH | 40° C., 75% RH |
| A | Eudragit L100-55 | 22 | Amorphous | Amorphous | Crystalline appeared |
| B | Eudragit L100-55 | 33 | Crystalline appeared | Amorphous | Amorphous |
| C | Eudragit L100-55 | 50 | Amorphous | Amorphous | Amorphous |
| D | HPMC-AS HG | 20 | Amorphous | Amorphous | Amorphous |
| E | HPMC-AS HG | 33 | Amorphous | Amorphous | Amorphous |
| F | HPMC-AS HG | 50 | Amorphous | Amorphous | Amorphous |

TABLE 6

| Summary of ASDs samples of Formula II at under stressed conditions over 12 days | | | | | |
|---|---|---|---|---|---|
| ASD ID | Polymer used | Drug loading | 25° C., 30% RH | 25° C., 75% RH | 40° C., 75% RH |
| A | Eudragit L100-55 | 22 | Amorphous | Amorphous | Amorphous |
| B | Eudragit L100-55 | 33 | Amorphous | Amorphous | Amorphous |
| C | Eudragit L100-55 | 50 | Amorphous | Amorphous | Amorphous |
| D | HPMC-AS HG | 20 | Amorphous | Amorphous | Amorphous |
| E | HPMC-AS HG | 33 | Amorphous | Amorphous | Amorphous |
| F | HPMC-AS HG | 50 | Amorphous | Amorphous | Amorphous |

Investigation of Target ASDs in Vehicle

Figure 4:
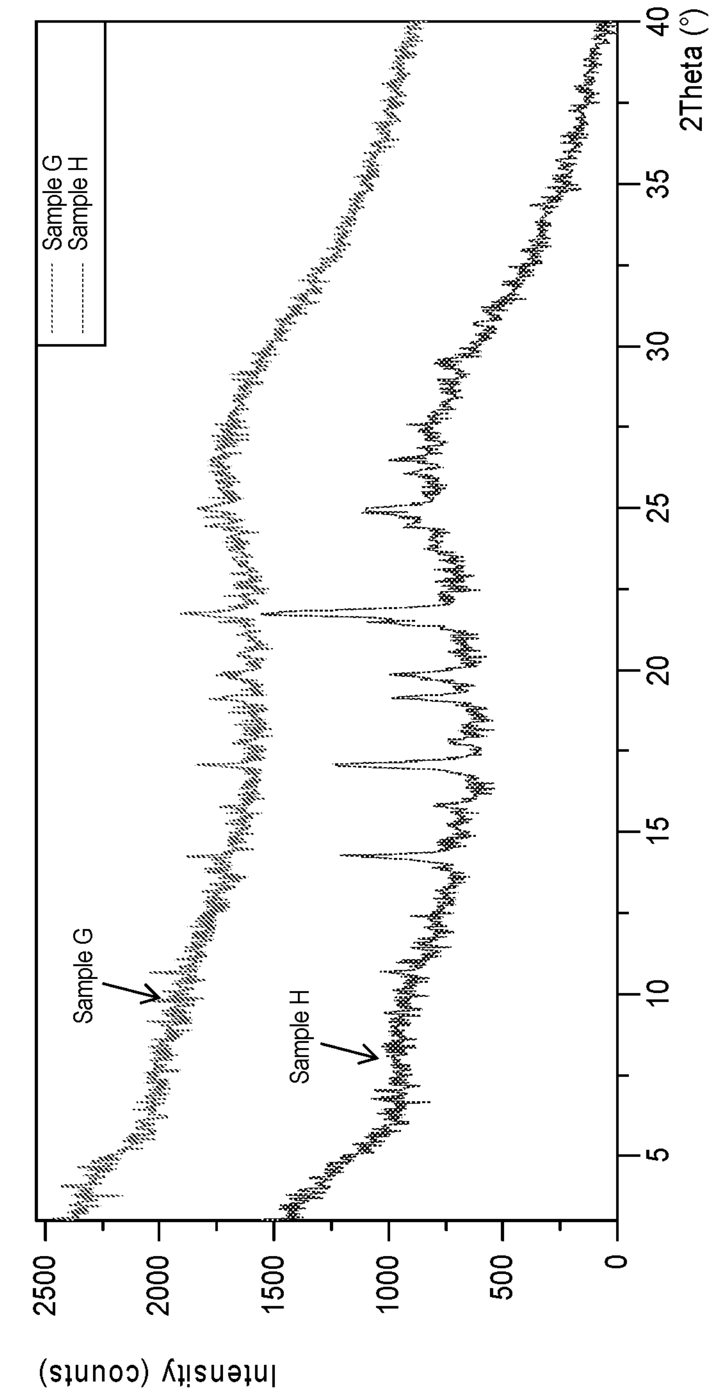
FIG. 4 shows an XRPD overlay of the two ASDs of Formula II after suspension in vehicle for 24 hours.
Figure 5:
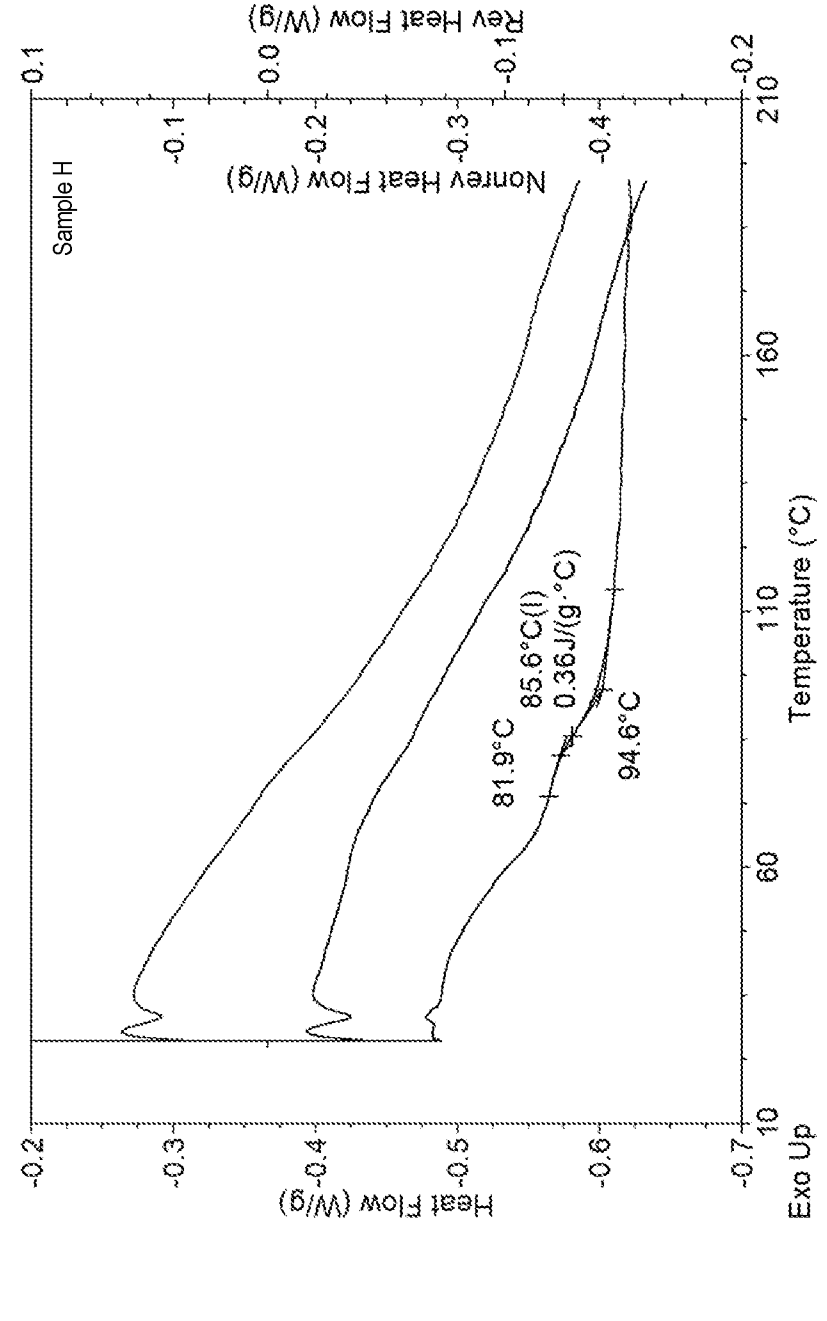

To establish a target ASD prototype, 50% drug loading Eudragit and 33% HPMCAS ASDs were suspended in a vehicle using 0.5% hydroxypropyl methylcellulose (HPMC E15) and 0.1% Tween 80. The stability and characterization results are summarized in Table 7. The solubility of using 33% HPMCAS-HG polymer was boosted at 2 hours. Also, ASD in HPMCAS exhibited better stability However, both ASDs gave crystalline material after 24 hours of suspension in the vehicle, shown in FIG. 4. Actual drug loading and Tg was measured for the 33% drug loading HPMCAS ASD, which contained 31.3% drug and a Tg of 85.6° C., as shown in FIG. 5.

TABLE 7

Summary of vehicle suspension test of ASDs of Formula II

| | 50% Eudragit ASD (Sample G) | 33% HPMC-AS ASD (Sample H) |
|---|---|---|
| ASD used (mg) | 98.9 | 150.5 |
| Vehicle used (mL) | 5.0 | 5.0 |
| API concentration in vehicle over 2 h (mg/mL) | 0.0353 | 0.0943 |
| Solid form in vehicle over 2 h | Crystalline material appeared | Amorphous (few crystalline materials appeared) |
| API concentration in vehicle over 24 h (mg/mL) | 0.096 | 0.115 |
| Solid form in vehicle over 24 h | Crystalline material appeared | Crystalline material appeared |
| Drug loading (HPLC) | N/A | 31.3% |
| Tg | N/A | 85.6° C. |

Example 3

Scale-Up and Characterization of ASD of Formula II with HPMCAS-HG

One batch of ASD (2.9963 g API, compound of Formula II, and 6.0004 g HPKCAS-HG) was prepared by spray drying (33% API loading) in ~100 mL acetone/water (4:6, v/v) as solvent. The batch was dried under vacuum at RT and then characterized by XRPD, TGA, mDSC, PLM and HPLC. 6.217 g ASD was obtained (69.1% yield). Results are summarized in Table 8.

Figure 6:
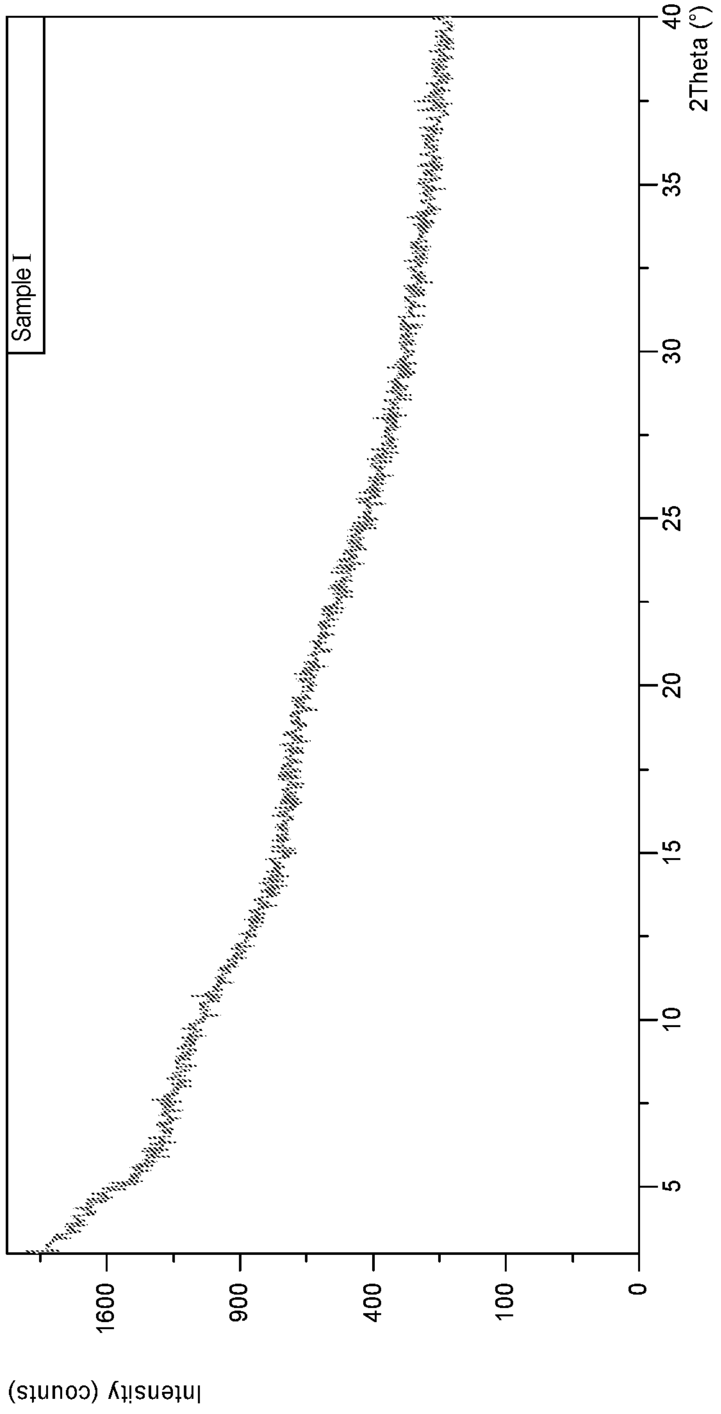
Figure 7:
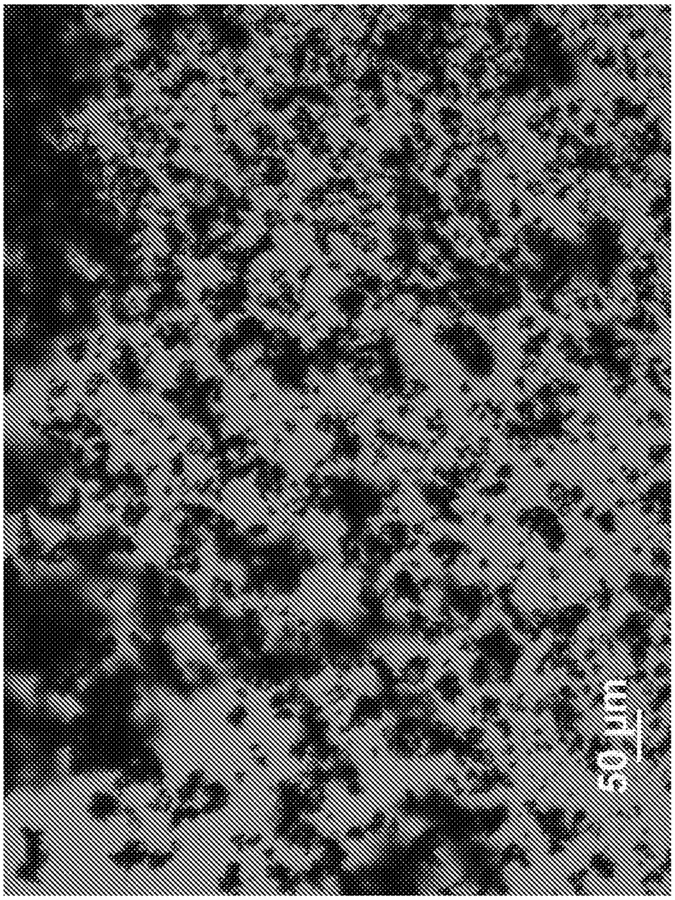
Figure 9:
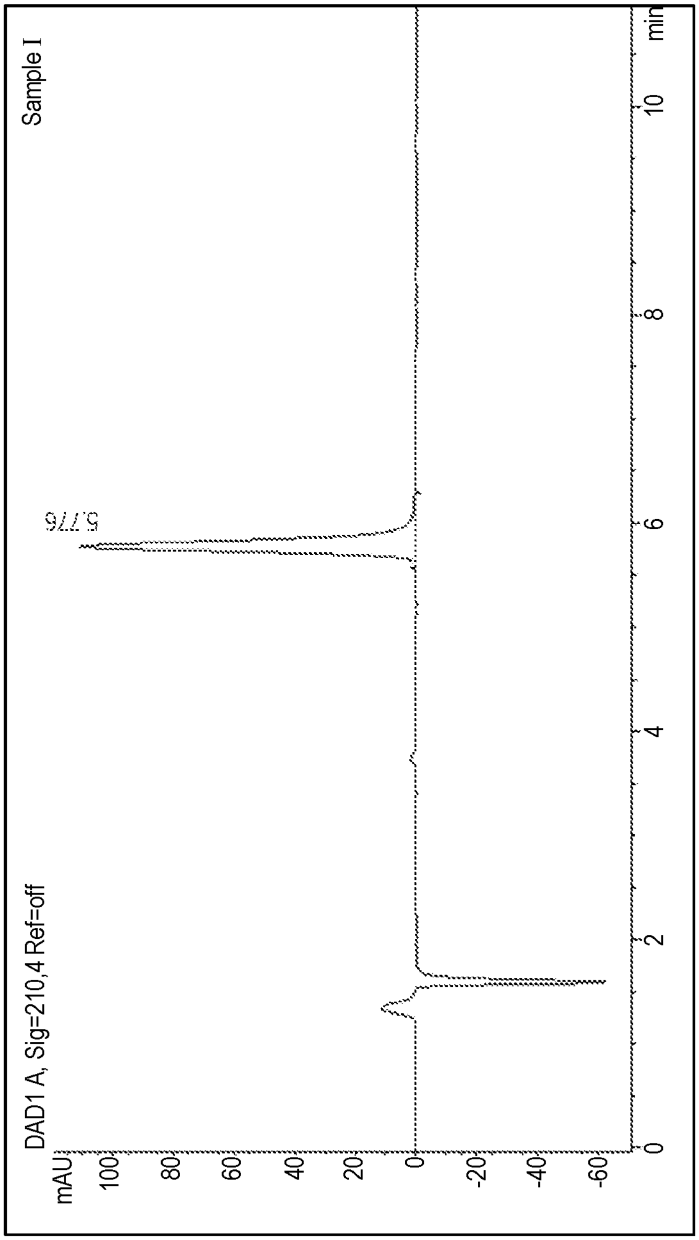
FIG. 9 shows a high performance liquid chromatography (HPLC) trace of sample of Formula II with 33% drug loading dispersed in HPMCAS-HG.

The XRPD results (FIG. 6) showed the ASD batch was amorphous. Fine particles were observed without birefringence was observed in PLM, as shown in FIG. 7. No weight loss up to 199° C. and a Tg at 86.5° C. (middle temperature) were observed by TGA/mDSC, as shown in FIG. 8. HPLC trace of the ASD shown in FIG. 9 yielded an actual drug loading of 31.2%.

TABLE 8

Characterization results of scaled-up ASD sample (API + HPMCAS-HG)

| Sample ID | Starting material | Yield (%) | Form | Weight loss (%) | Tg (° C.)* | Morphology | % API by HPLC |
|---|---|---|---|---|---|---|---|
| Sample I | Formula II | 69.1 | Amorphous | Negligible (to 199° C.) | 86.5 | Fine particles | 31.2 |

*Middle temperature.

Example 4

Formulation Development for Formula III (I) Preparation of ASDs

Figure 10:
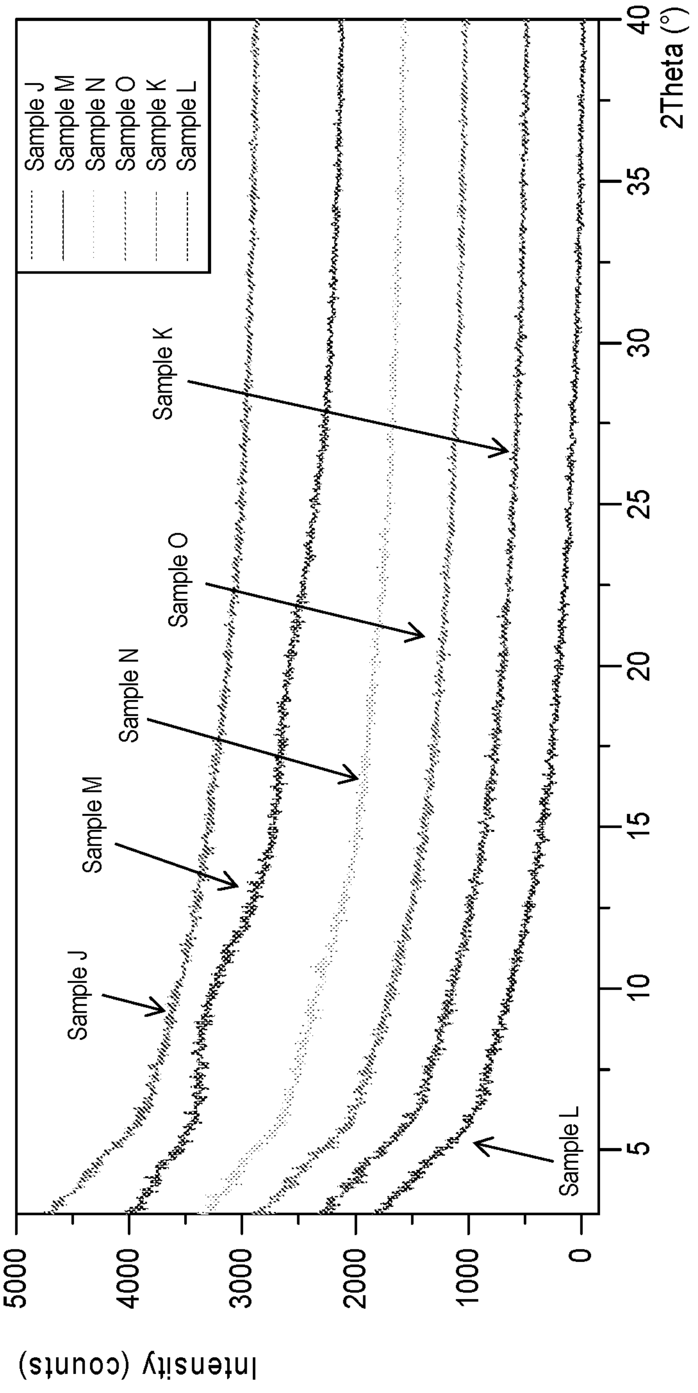
FIG. 10 shows XRPD overlay of six ASDs of Formula III.
Figure 11A:
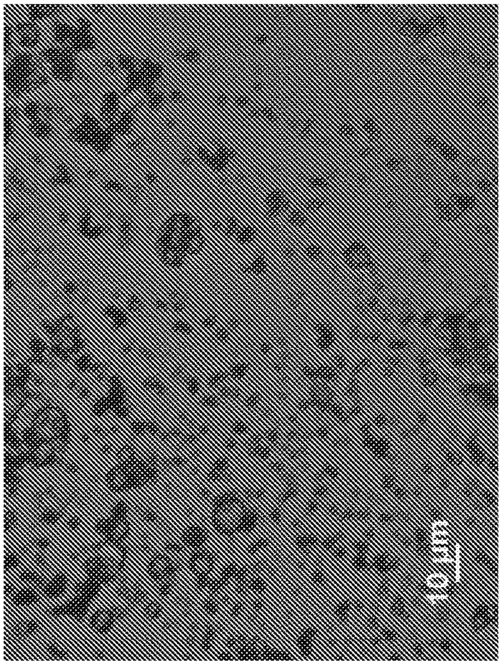
FIG. 11 shows PLM images of ASD of Formula III.
Figure 11B:
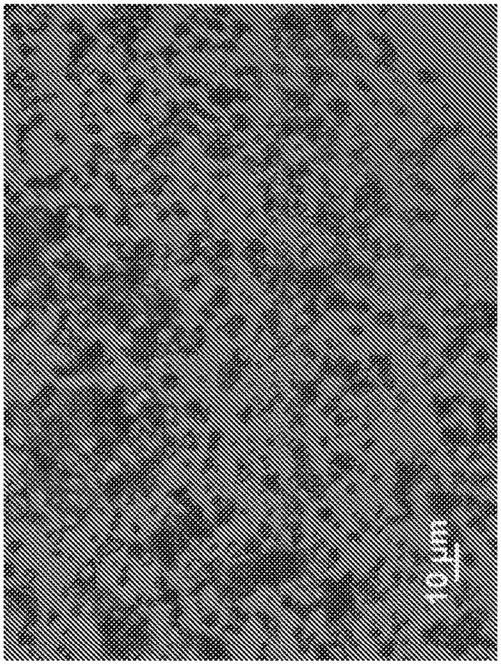
Figure 11C:
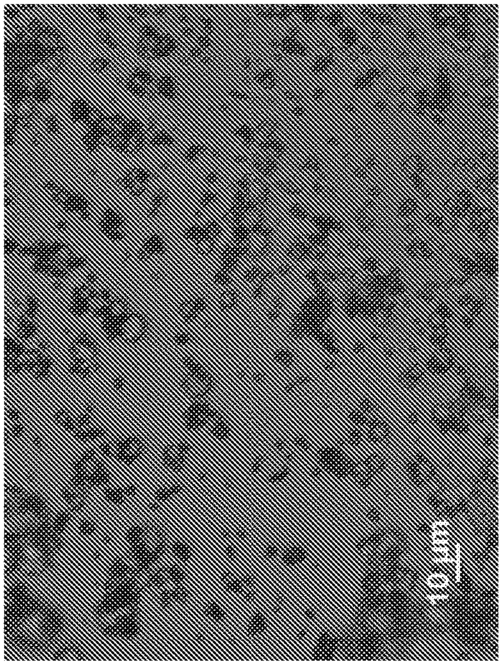
Figure 11D:
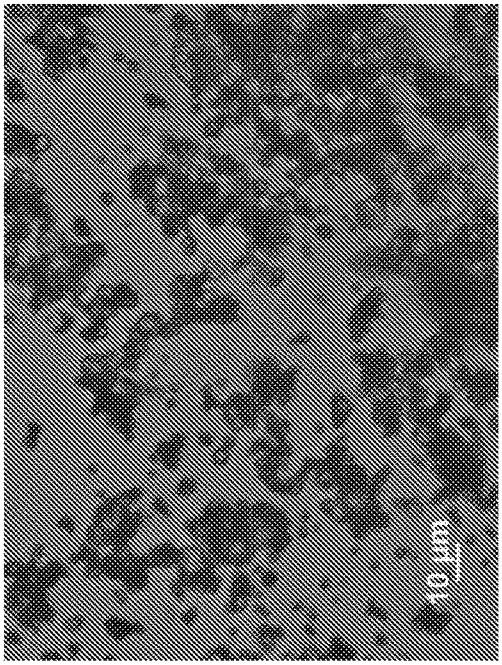
Figure 12:
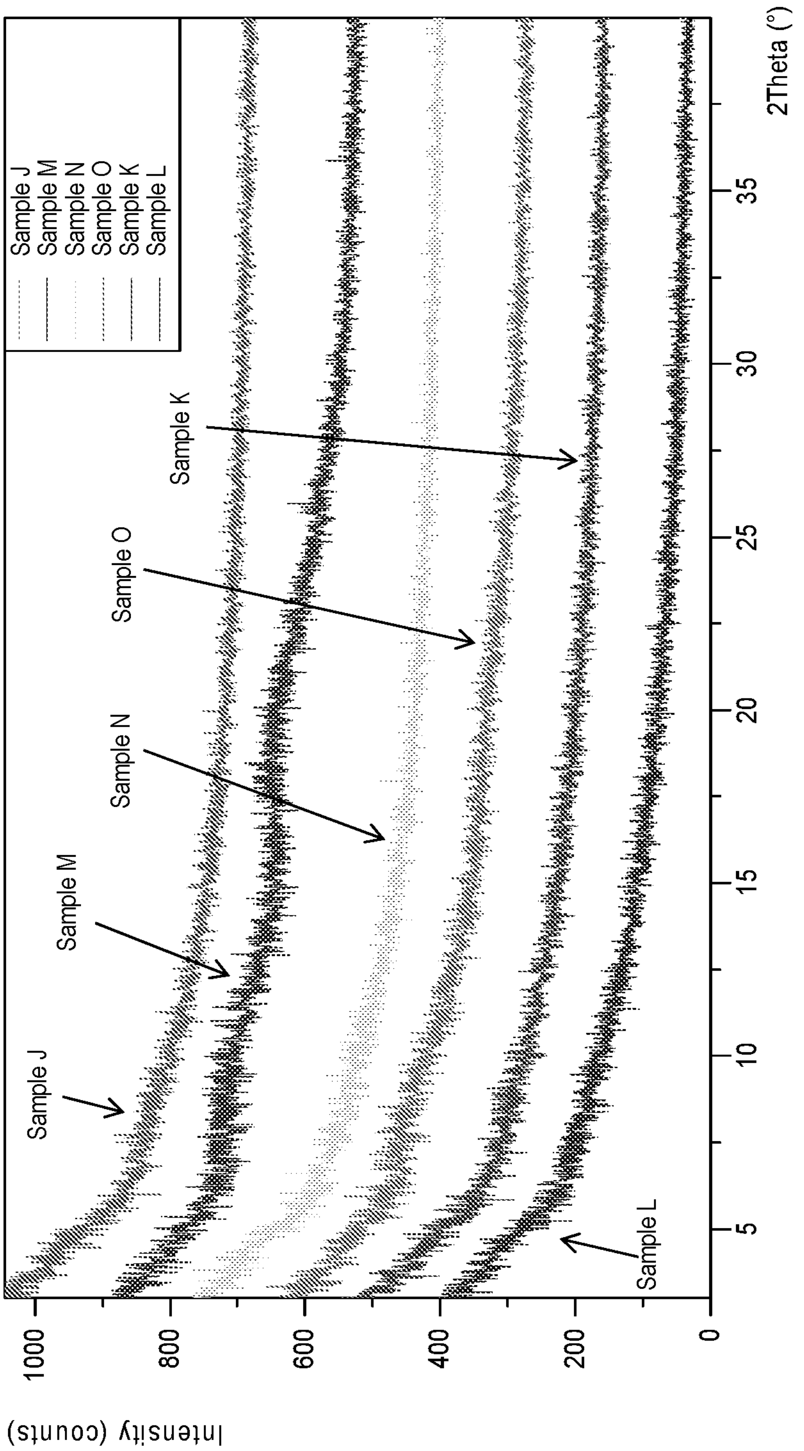
FIG. 12 shows XRPD overlay of six ASDs of Formula III after 12 days in 40° C./75% RH.

ASDs of 20%, 33%, and 50% API in excipients (HPMCAS-HG, Eudragit L100-55) were prepared by spray drying. About 0.4-0.8 g API material and corresponding excipient were weighed into a glass vial followed by addition of about 80 mL acetone/water (4:6, v/v) to dissolve the solids (acetone used first, then added water). The inlet temperature for spray drying was set as 150° C. and the outlet temperature was measured around 70° C. The ASDs were characterized by XRPD, FIG. 10. The results are summarized in Table 9. PLM images are displayed in FIG. 11 *a* through FIG. 11*d* show all the ASD samples were made of fine particles without birefringence.

TABLE 9

Characterization summary of ASD samples of Formula III

| Sample ID | Excipient | Yield (%) | Amorphous? | Yield (%) |
|---|---|---|---|---|
| J | Eudragit L100-55 | 20 | Y | 36 |
| K | Eudragit L100-55 | 33 | Y | 32 |
| L | Eudragit L100-55 | 50 | Y | 41 |
| M | HPMC-AS HG | 20 | Y | 54 |
| N | HPMC-AS HG | 33 | Y | 39 |
| O | HPMC-AS HG | 50 | Y | 45 |

(II) Evaluation of ASDs of Formula III Under Stressed Conditions

Figure 23A:
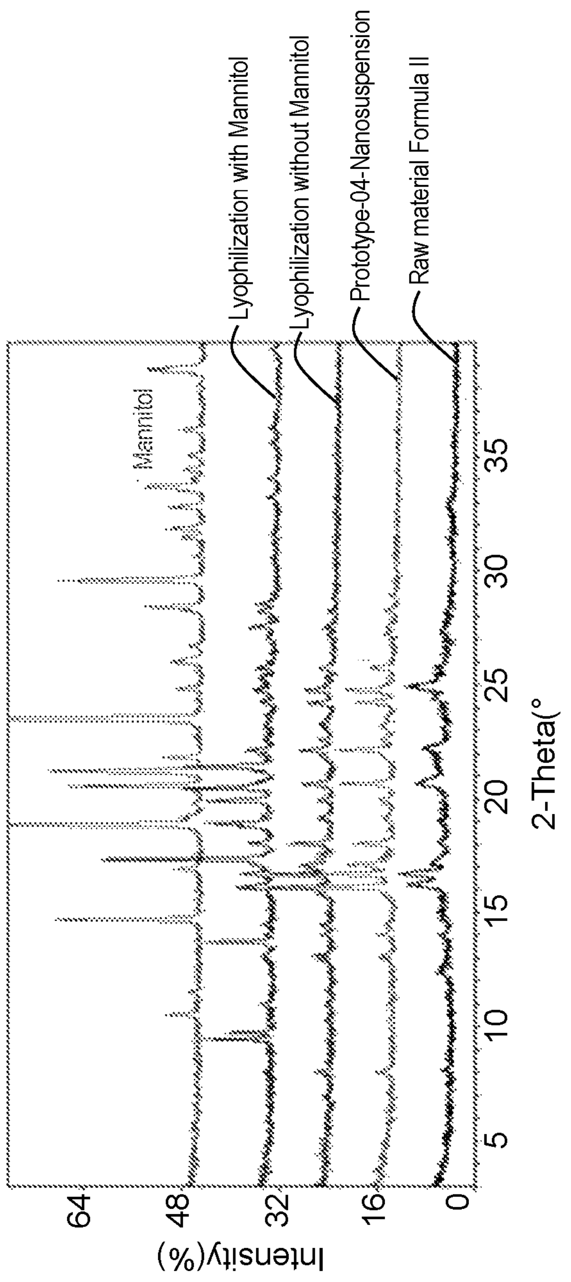
FIG. 23 (*a*) shows lyophilized powder reconstitution study and stability test for Formula III and (b) lyophilized powder after reconstitution in water.
Figure 23B:
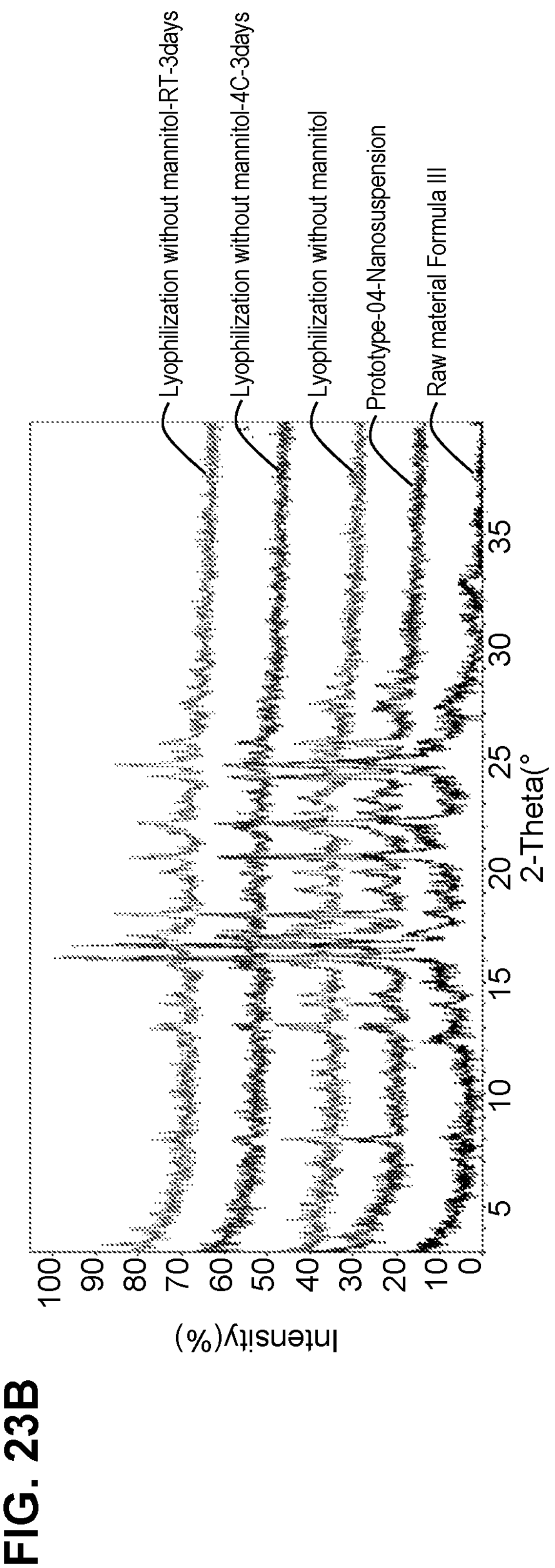

The stability of the six ASDs were evaluated in three stations (25° C./30% RH, 25° C./75% RH, 40° C./75% RH) over 5 days and 12 days (Table 10 and Table 11, respectively). The XRPD pattern overlay of the six ASDs under stressed conditions at 40° C./75% RH over 12 days are shown in FIG. 23. ASDs prepared with both polymers exhibited good physical stability, as no apparent crystalline materials were observed via XRPD.

TABLE 10

Summary of ASDs of Formula III under stressed conditions over 5 days

| ASD ID | Polymer used | Drug loading | 25° C., 30% RH | 25° C., 75% RH | 40° C., 75% RH |
|---|---|---|---|---|---|
| J | Eudragit L100-55 | 22 | Amorphous | Amorphous | Amorphous |
| K | Eudragit L100-55 | 33 | Amorphous | Amorphous | Amorphous |
| L | Eudragit L100-55 | 50 | Amorphous | Amorphous | Amorphous |

TABLE 10-continued

Summary of ASDs of Formula III under stressed conditions over 5 days

| ASD ID | Polymer used | Drug loading | 25° C., 30% RH | 25° C., 75% RH | 40° C., 75% RH |
|---|---|---|---|---|---|
| M | HPMC-AS HG | 20 | Amorphous | Amorphous | Amorphous |

TABLE 10-continued

Summary of ASDs of Formula III under stressed conditions over 5 days

| ASD ID | Polymer used | Drug loading | 25° C., 30% RH | 25° C., 75% RH | 40° C., 75% RH |
|---|---|---|---|---|---|
| N | HPMC-AS HG | 33 | Amorphous | Amorphous | Amorphous |
| O | HPMC-AS HG | 50 | Amorphous | Amorphous | Amorphous |

TABLE 11

Summary of ASDs of Formula III under stressed conditions over 12 days

| ASD ID | Polymer used | Drug loading | 25° C., 30% RH | 25° C., 75% RH | 40° C., 75% RH |
|---|---|---|---|---|---|
| J | Eudragit L100-55 | 22 | Amorphous | Amorphous | Amorphous |
| K | Eudragit L100-55 | 33 | Amorphous | Amorphous | Amorphous |
| L | Eudragit L100-55 | 50 | Amorphous | Amorphous | Amorphous |
| M | HPMC-AS HG | 20 | Amorphous | Amorphous | Amorphous |
| N | HPMC-AS HG | 33 | Amorphous | Amorphous | Amorphous |
| O | HPMC-AS HG | 50 | Amorphous | Amorphous | Amorphous |

Investigation of Target ASDs of Formula III in Vehicle

Figure 13:
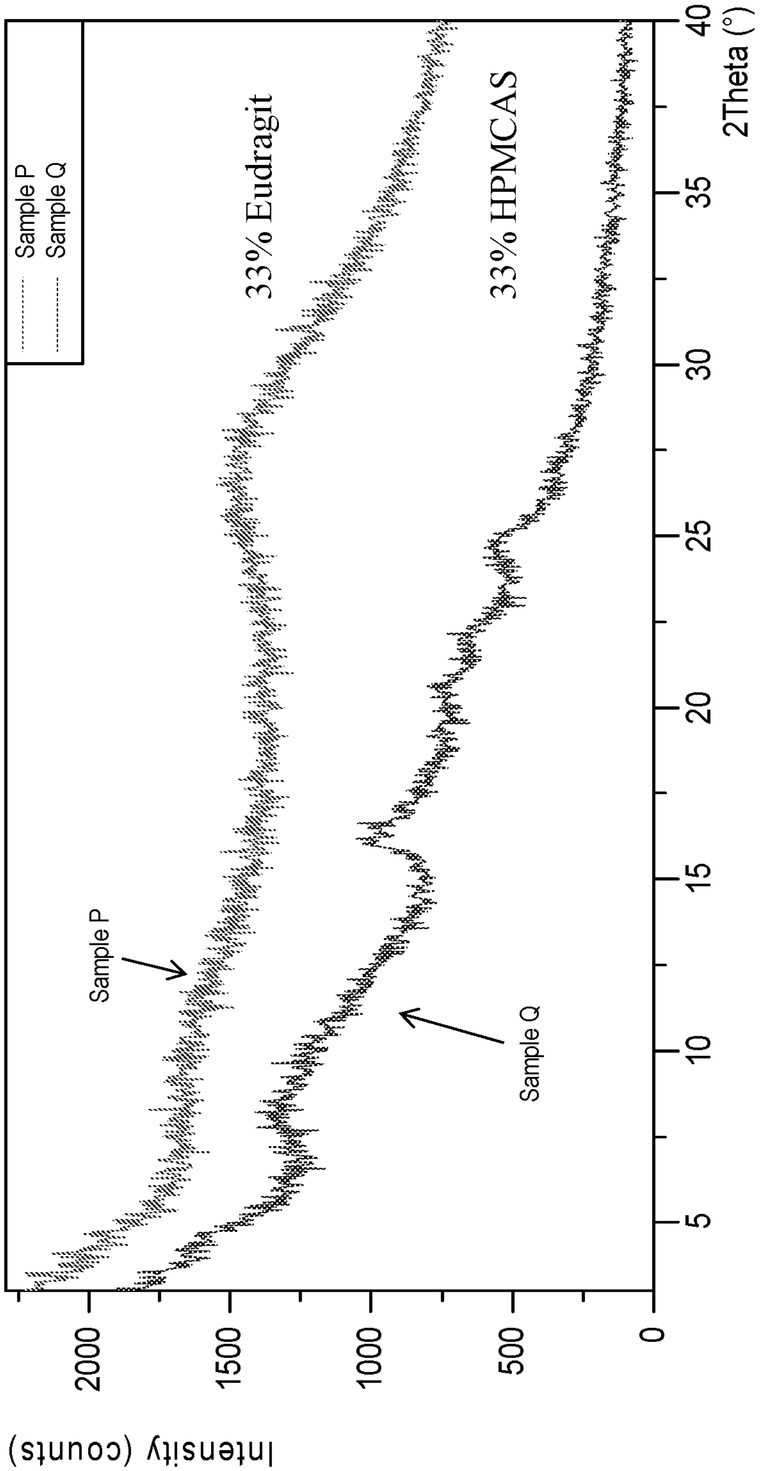
FIG. 13 shows XRPD overlay of ASDs of Formula III after suspension in vehicle for 24 hours.
Figure 14:
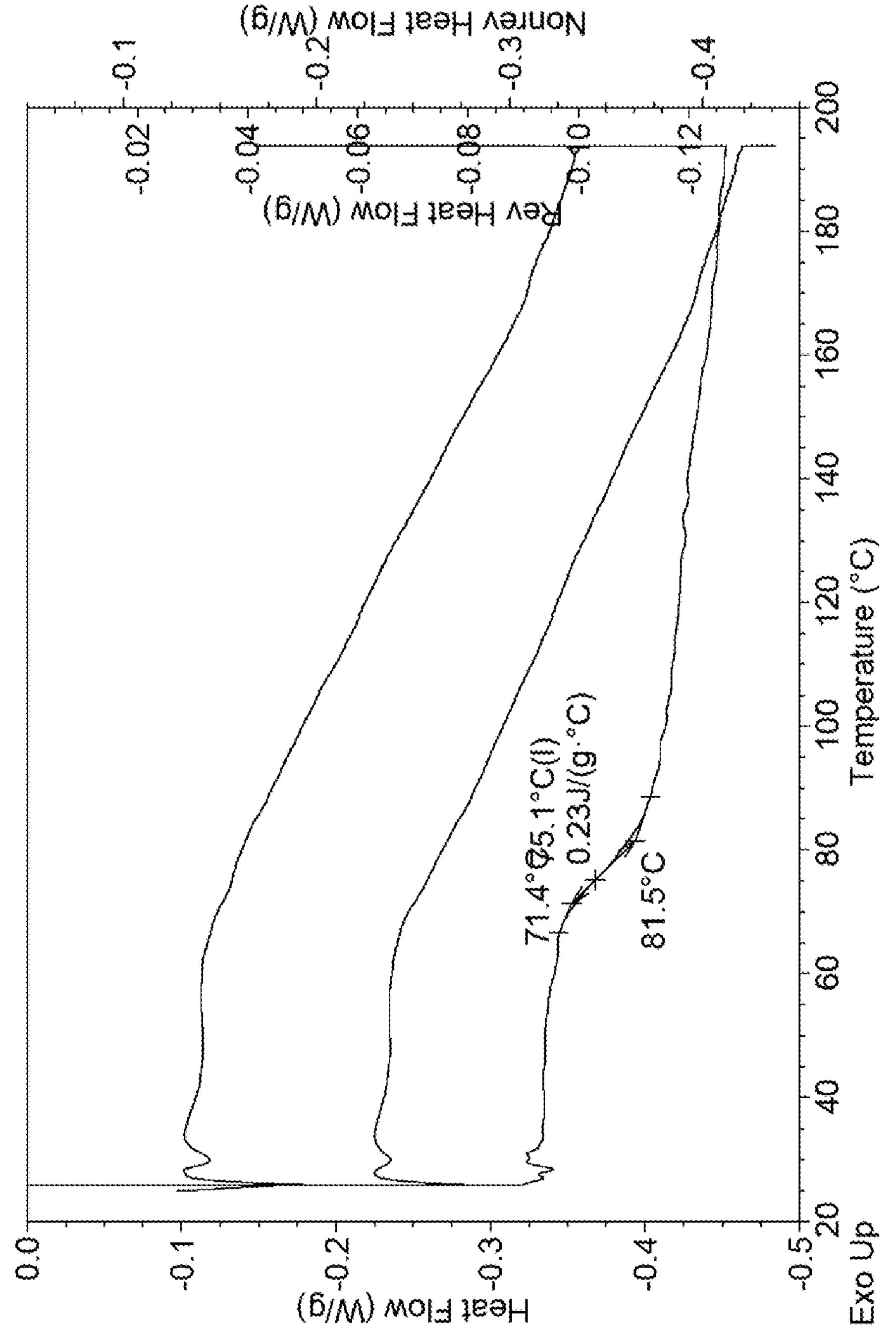

To establish a target ASD prototype, 33% drug loading Eudragit and 33% HPMCAS ASDs were suspended in a vehicle using 0.5% hydroxypropyl methylcellulose (HPMC E15) and 0.1% Tween 80. The stability and characterization result are summarized in Table 12. The solubility of using 33% HPMCAS-HG polymer was boosted at 2 hours Both ASDs gave crystalline material after 24 hour suspension in the vehicle, shown in FIG. 13. Actual drug loading and Tg was measured for the 33% drug loading HPMCAS ASD, which contained 31.4% drug and a Tg of 75.1° C., as shown in FIG. 14.

TABLE 12

Summary of vehicle suspension test of ASDs of Formula III

| | 33% Eudragit ASD Sample P4 | 33% HPMC-AS ASD Sample Q4 |
|---|---|---|
| ASD used (mg) | 150.3 | 149.0 |
| Vehicle used (mL) | 5.0 | 5.0 |
| API concentration in vehicle over 2 h (mg/mL) | 0.037455 | 0.07044 |
| Solid form in vehicle over 2 h | Amorphous | Amorphous |
| API concentration in vehicle over 24 h (mg/mL) | 0.092 | 0.028 |

TABLE 12-continued

Summary of vehicle suspension test of ASDs of Formula III

| | 33% Eudragit ASD Sample P4 | 33% HPMC-AS ASD Sample Q4 |
|---|---|---|
| Solid form in vehicle over 24 h | Crystalline material appeared | Crystalline material appeared |
| Drug loading (HPLC) | N/A | 31.4% |
| Tg | N/A | 75.1° C. |

Example 5

Scale-Up and Characterization of ASD of Formula III Dispersed in HPMCAS-HG

Figure 15:
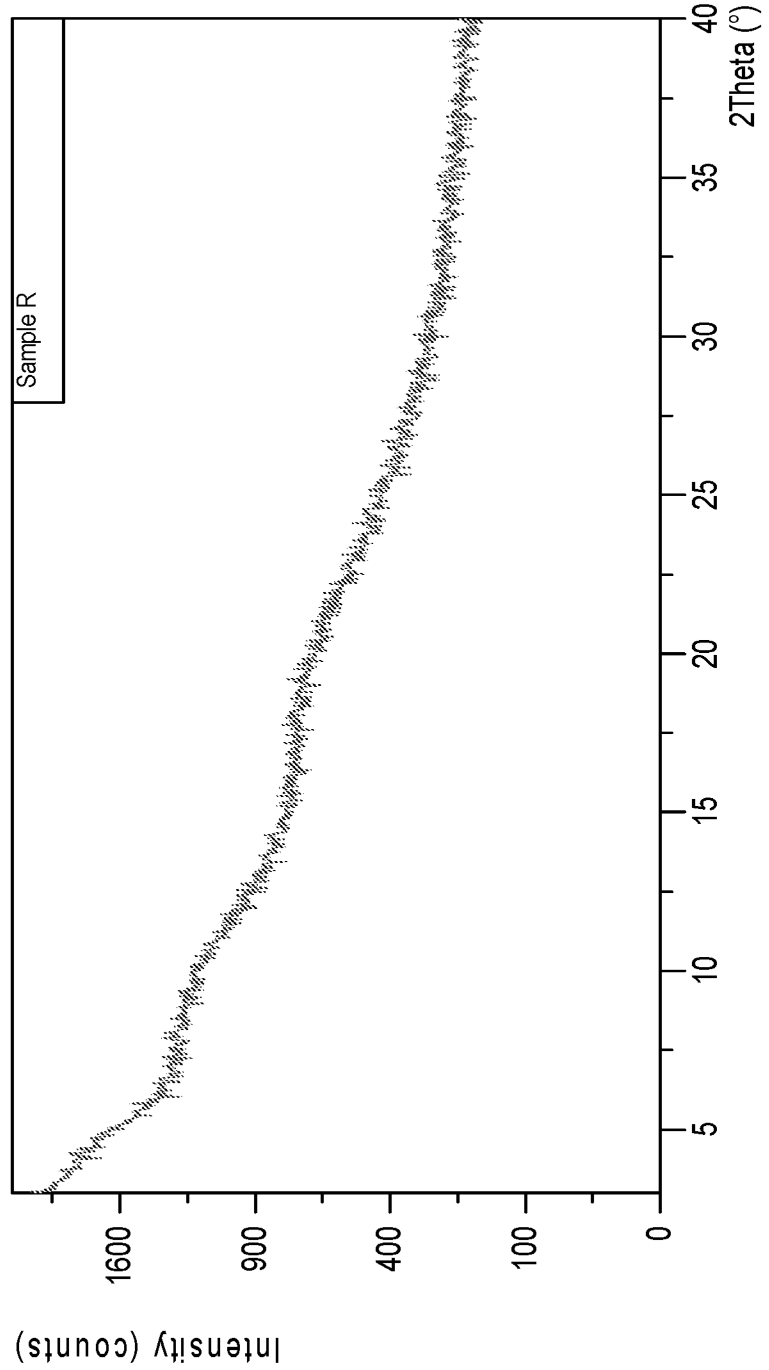
FIG. 15 shows XRPD overlay of ASDs of Formula III with 33% drug loading dispersed in HPMC-AS).
Figure 16:
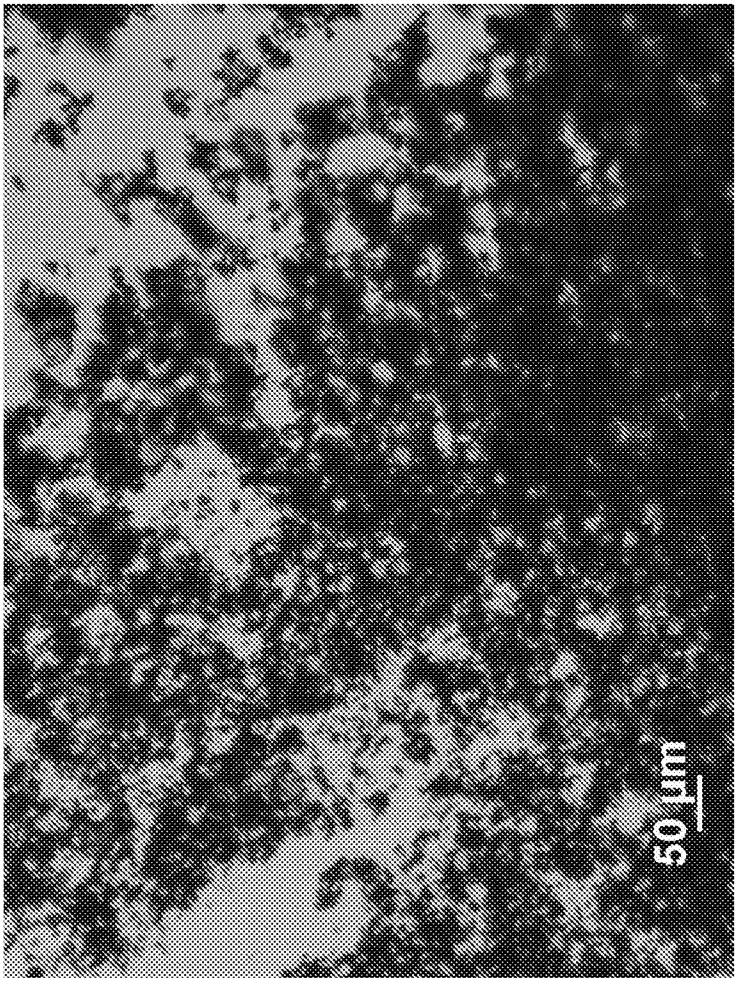
FIG. 16 shows PLM image of ASD of Formula III with (33% drug loading dispersed in HPMC-AS).
Figure 17:
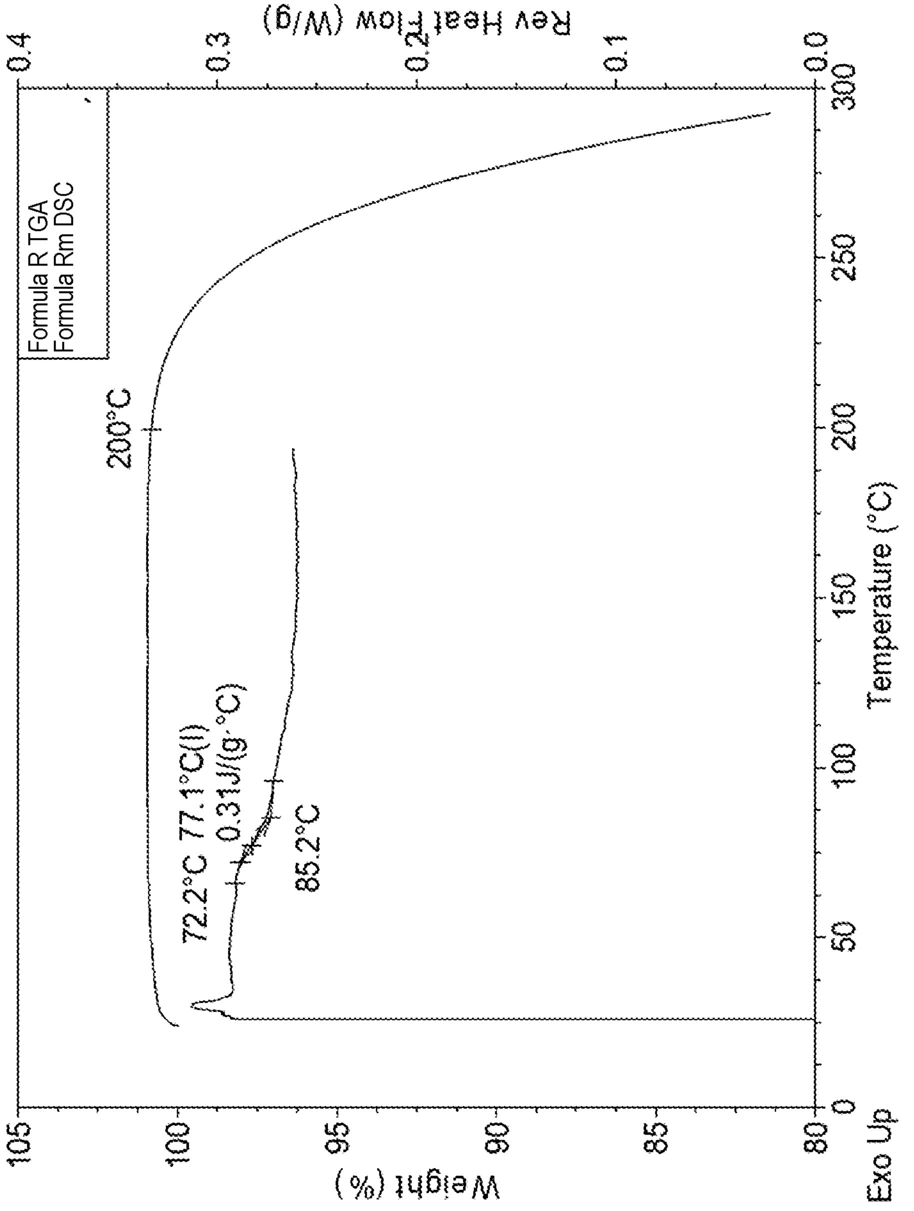
FIG. 17 shows TGA/mDSC curves of ASD sample of Formula III (a) 6021274-17 (33% drug loading with HPMC-AS).
Figure 18:
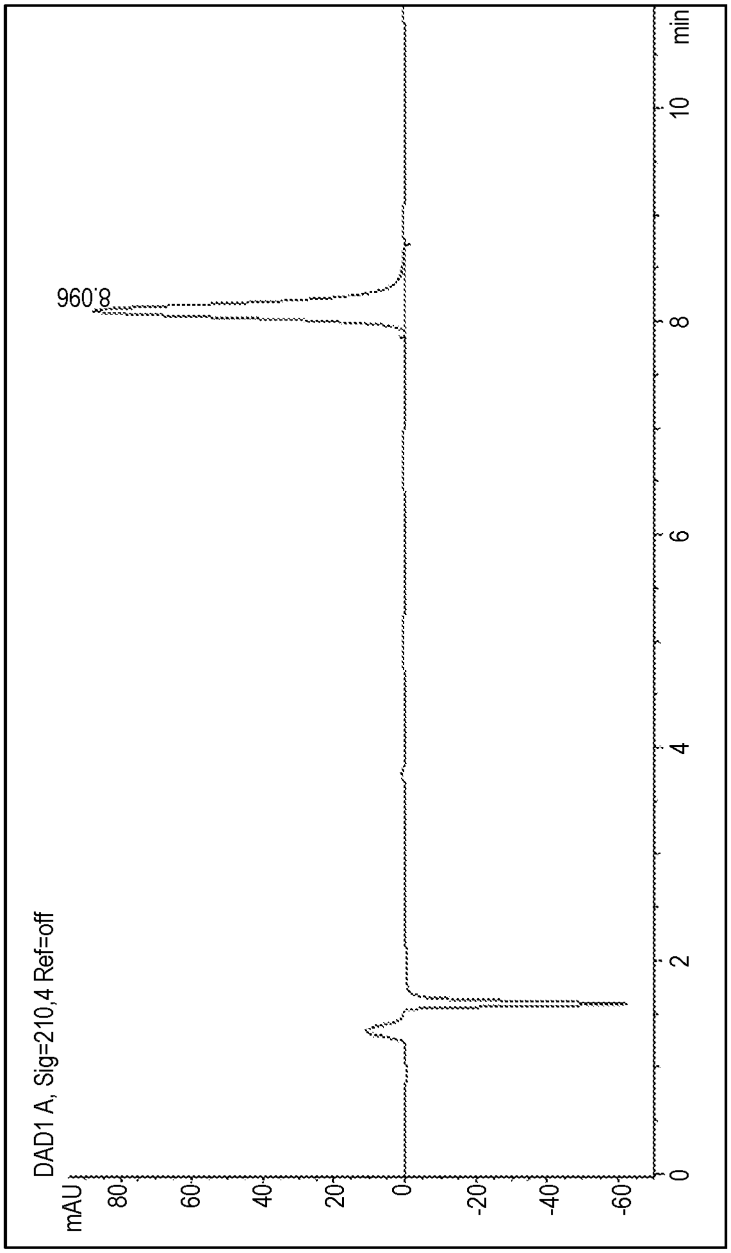
FIG. 18 shows HPLC trace of ASD sample of Formula III (a) 6021274-17 (33% drug loading with HPMC-AS).

One batch of ASD (3.012 g API, compound of Formula III, and 6.016 g HPMCAS-HG) was prepared by spray drying (33% API loading) in ~150 mL acetone/water (4:6, v/v) as solvent. The batch was dried under vacuum at RT and then characterized by XRPD, TGA, mDSC, PLM and HPLC. 4.181 g ASD was obtained (46.4% yield). Results are summarized in Table 13. The XRPD results in FIG. 15 showed that the ASD is amorphous. Fine particles were observed without birefringence was observed in PLM, as shown in FIG. 16. No weight loss up to 200° C. and a Tg at 77.1° C. (middle temperature) were observed by TGA/mDSC, as shown in FIG. 17. HPLC trace of the ASD shown in FIG. 18 yielded an actual drug loading of 31.4% (area=890.3, time=8.10 min).

TABLE 13

Characterization results of scaled-up ASD sample of Formula III dispersed in HPMCAS-HG)

| Sample ID | Starting material | Yield (%) | Form | Weight loss (%) | Tg (° C.)* | Morphology | % API by HPLC |
|---|---|---|---|---|---|---|---|
| Sample R | Formula III | 46.1 | Amorphous | Negligible (to 200° C.) | 77.1 | Fine particles | 31.4 |

*Middle temperature.

Example 6

General Methods of Nanosuspension Instrumental Measurements

XRPD patterns were measured on a Bruker PDS-PF-XRD-01 X-ray powder diffractometer using Cu-kα radiation. The tube voltage and amperage were set to 40 kV and 40 mA, respectively. A two-theta (2θ°) scanning rate of 10°/min with a scan scope ranging from 3° to 40° was used. TGA and DSC data were collected using a TA Q2000 using a 10° C./min heating range (temperature range from RT to 300° C.) in an $N_2$ atmosphere. Roller mixing was carried out using a Stoneware 755 RMV. A Nicomp 380/ZLS was used for zeta potential and particle size measurements.

Example 7

Physical Characterization of Starting Materials

Figure 19A:
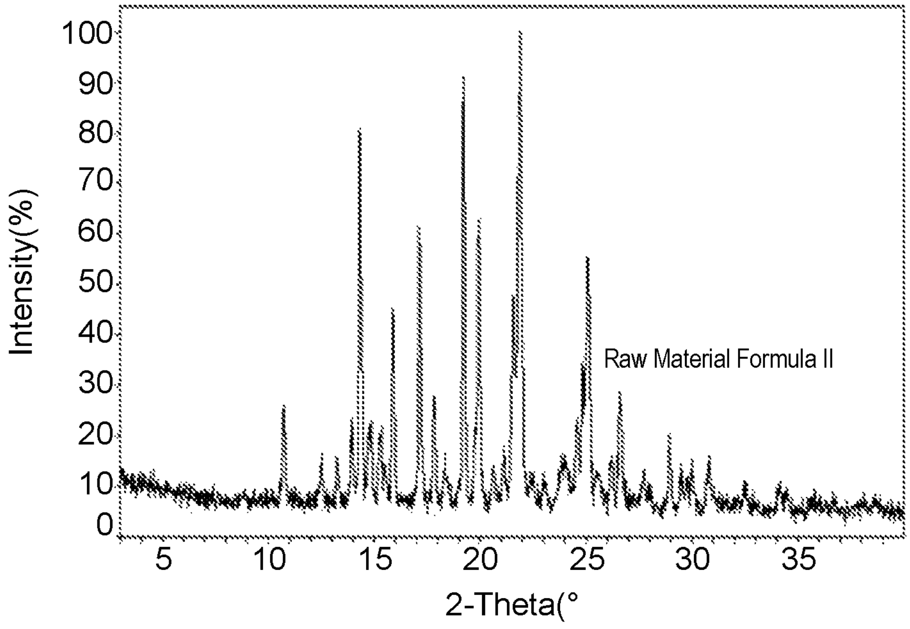
FIG. 19 shows XRPD pattern of (a) compound of Formula II used as starting material in the preparation of ASD and (b) compound of Formula III used as starting material in the preparation of nanosuspensions.
Figure 19B:
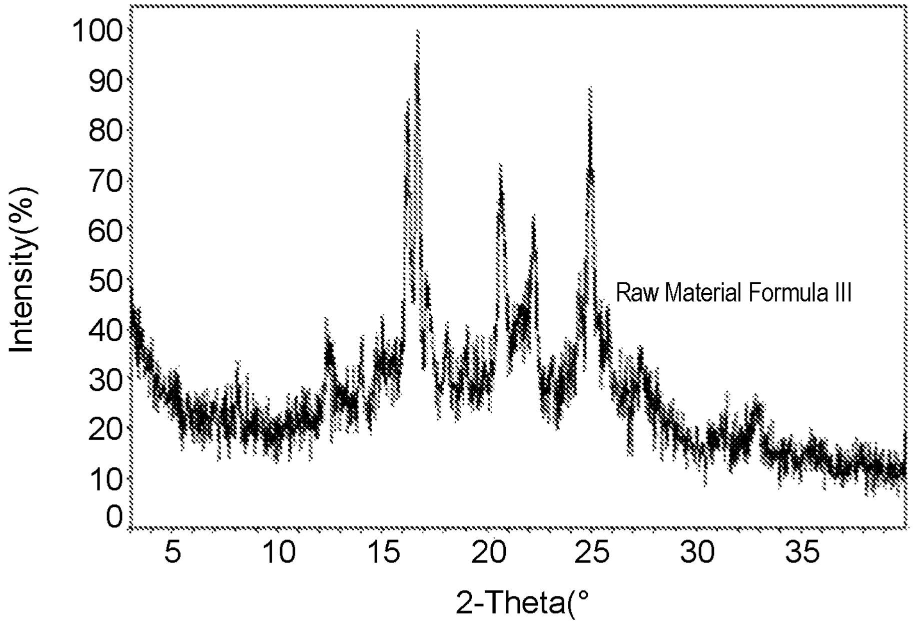
Figure 20A:
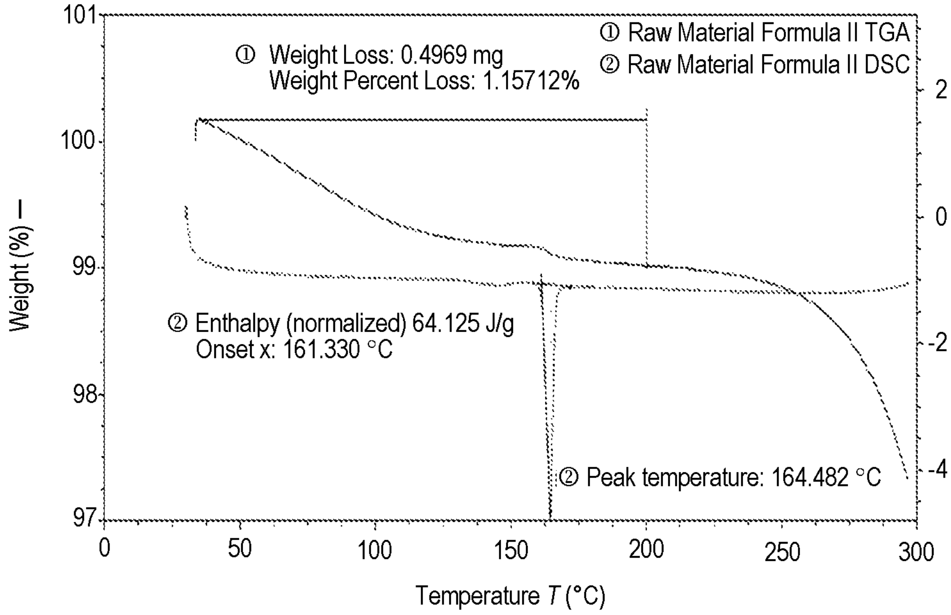
FIG. 20 shows TGA and DSC overlays for (a) compound of Formula II used as starting material in the preparation of ASD and (b) compound of Formula III used as starting material in the preparation of nanosuspensions.
Figure 20B:
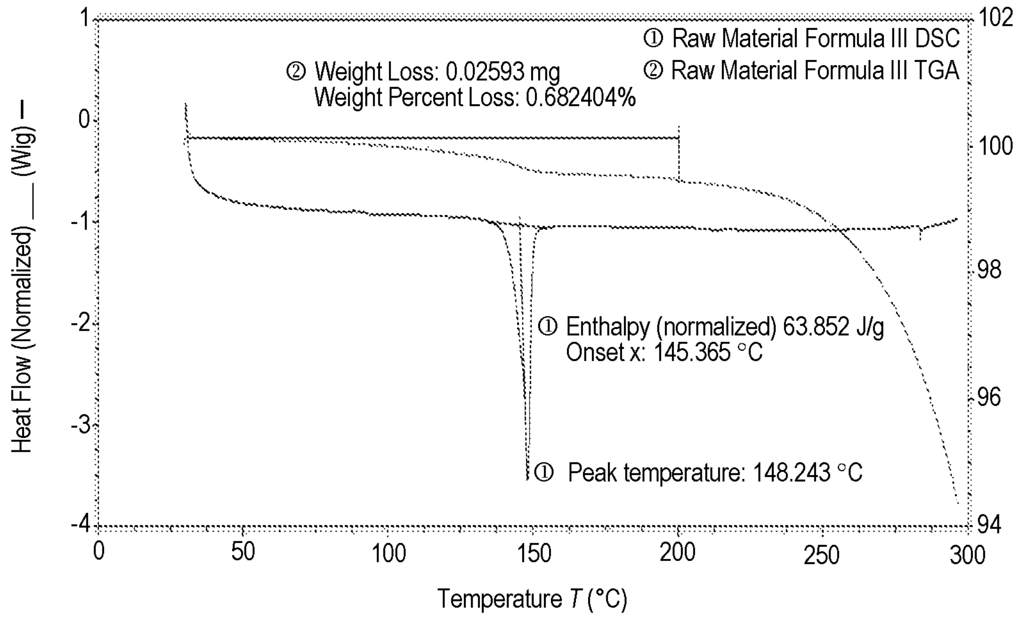
Figure 21A:
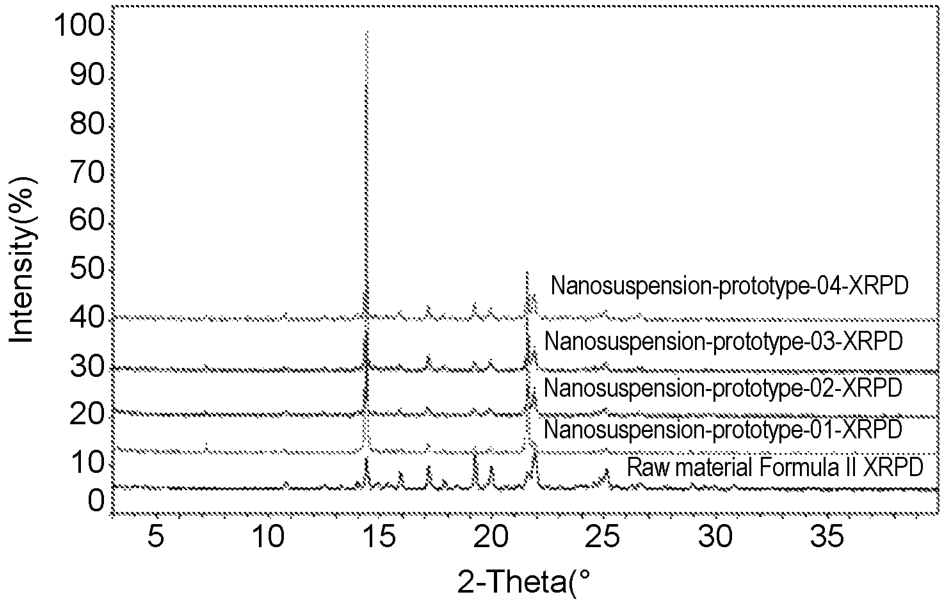
FIG. 21 shows XRPD overlays of nanosuspensions for (a) Formula II and (b) Formula III.
Figure 21B:
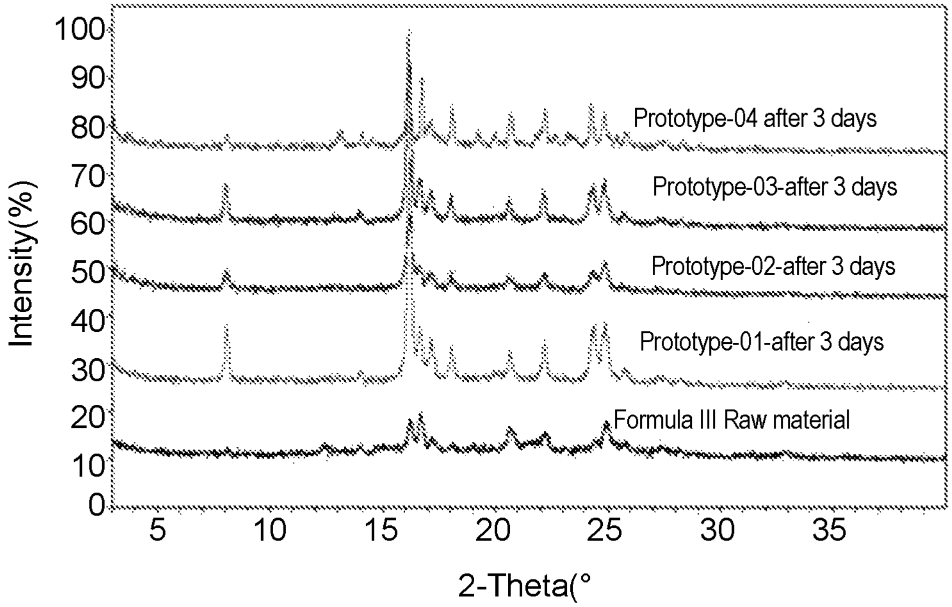
Figure 22A:
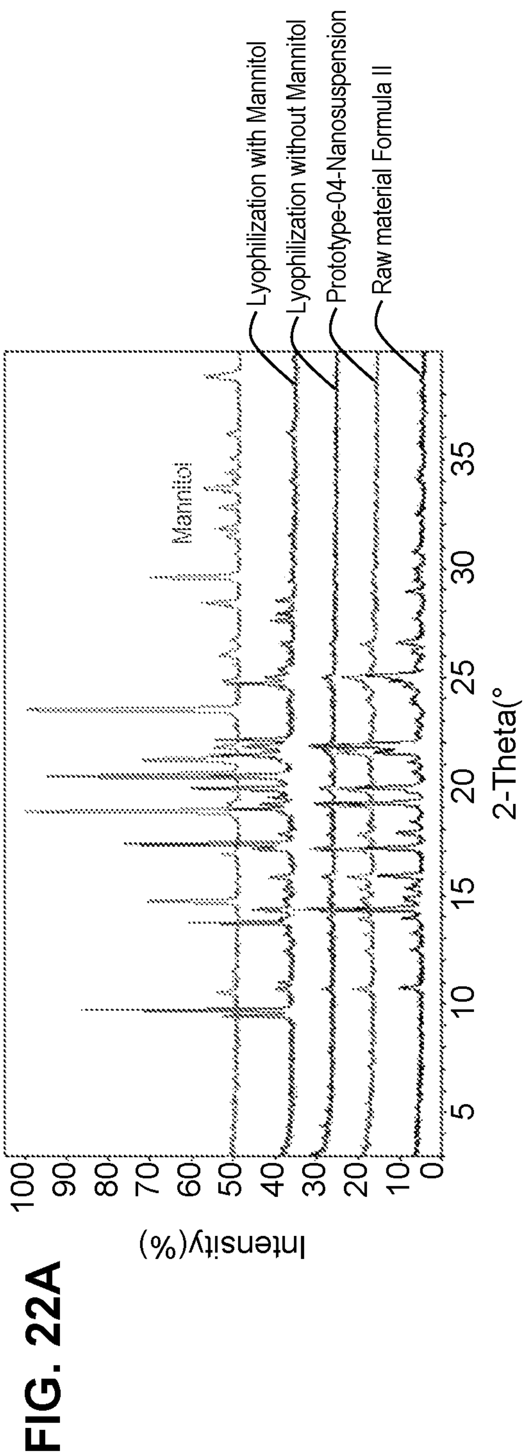
FIG. 22 (*a*) shows lyophilized powder reconstitution study and stability test for Formula II and (b) lyophilized powder after reconstitution in water.
Figure 22B:
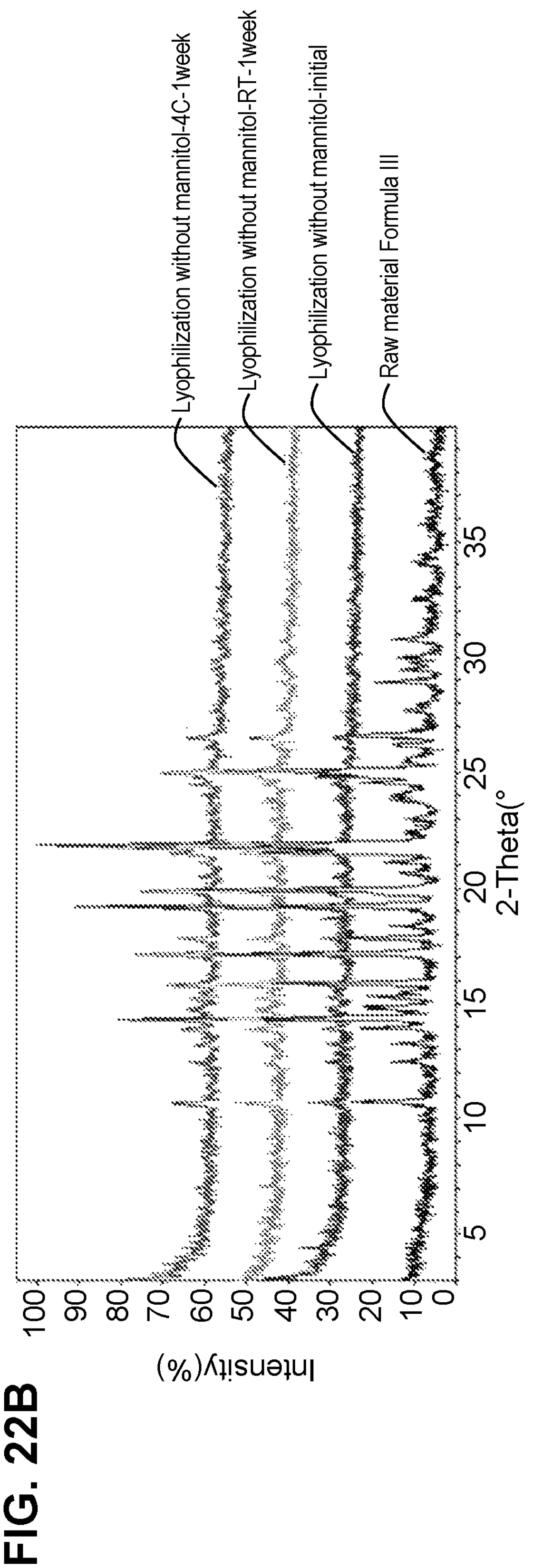

The raw material of Formula II and Formula III were characterized by XRPD, TGA, and DSC. The XRPD results indicated that the starting material was crystalline, as shown in FIGS. 19*a* and 19*b*. TGA and DSC results for Formula II showed that the starting material exhibited a weight loss of 1.1571% in total up to 200° C. and an endothermic peak at 161.33° C., as shown in FIG. 20*a*. TGA and DSC results for Formula III showed that the starting material exhibited a weight loss of 0.6824% in total up to 200° C. and an endothermic peak at 145.365° C., as shown in FIG. 20*b*.

Example 8

Preparation of Nanosuspensions

Nanosuspensions were prepared with four different vehicles (0.5% HPMC E5/0.5% Tween® 80, 0.5% HPMC E5/0.5% PVP K30/0.2% SLS, 0.5% HPMC E5/0.5% PVP K30/0.5% Tween® 80, and. 1% Poloxamer 188/0.5% Tween® 80). Briefly, 50 mg of active pharmaceutical ingredient (API) was weighed into a 30 mL bottle and 0.5 mL of 0.5% hydroxypropyl methylcellulose (HPMC) E5/0.5% Tween® 80 was added. Then 0.25 mL or 0.5 mL of 0.8 mm zirconium beads were added. The bottle was put onto roller mixer for continuous milling (up to 3 days). The obtained nanosuspensions for Formula II and Formula III were characterized by particle size distribution (PSD), appearance, pH, purity and physical form as noted in Table 14 and Table 15. XRPD results are shown in FIG. FIG. 20*a* and FIG. 20*b*.

TABLE 14

Characterization of Formula II nanosuspensions

| Vehicle No. | Vehicle (w/v, %) | Appearance | pH | PSD (D90, nm) | Conc., mg/mL | Purity % | Form Change (XRPD) |
|---|---|---|---|---|---|---|---|
| 1 | 0.5% HPMC E5/0.5% Tween80 | Homogeneous suspension | 6.82 | 385.3 | 84.82 | 99.4 | Same to initial |
| 2 | 0.5% HPMC E5/0.5% PVP K30/0.2% SLS | | 6.87 | 310.9 | 84.39 | 99.4 | |
| 3 | 0.5% HPMC E5/0.5% PVP K30/0.5% Tween80 | | 5.19 | 377.5 | 81.00 | 99.4 | |
| 4 | 1% Poloxamer 188/0.5% Tween80 | | 6.00 | 281.0 | 87.38 | 99.4 | |

TABLE 15

Characterization of Formula III nanosuspensions

| Vehicle No. | Vehicle (w/v, %) | Appearance | pH | PSD (D90, nm) | Conc., mg/mL | Purity % | Form Change (XRPD) |
|---|---|---|---|---|---|---|---|
| 1 | 0.5% HPMC E5/0.5% Tween80 | Homogeneous suspension | 6.82 | 693.0 | 52.5 | 100.0 | Same to initial |
| 2 | 0.5% HPMC E5/0.5% PVP K30/0.2% SLS | | 7.29 | 513.9 | 54.3 | 100.0 | |
| 3 | 0.5% HPMC E5/0.5% PVP K30/0.5% Tween80 | | 7.19 | 709.1 | 51.0 | 100.0 | |
| 4 | 1% Poloxamer 188/0.5% Tween80 | | 7.09 | 376.4 | 55.8 | 100.0 | |

Example 9

Nanosuspension Stability Evaluation

Stability measurements for the nanosuspensions were evaluated at 3 days and 7 days under two different conditions (room temperature and 4° C.). Stability results for Formula II nanosuspensions are shown in Table 16. Stability results for Formula III nanosuspensions are shown in Table 17.

TABLE 16

Stability of Formula II nanosuspensions

| | | Prototype 1 | Prototype 2 | Prototype 3 | Prototype 4 |
|---|---|---|---|---|---|
| Initial | PSD (D90, nm) | 385.3 | 310.9 | 377.5 | 281.0 |
| | Appearance | Homogeneous suspension | Homogeneous suspension | Homogeneous suspension | Homogeneous suspension |
| | pH | 6.82 | 6.87 | 5.19 | 6.00 |

TABLE 16-continued

Stability of Formula II nanosuspensions

| | | Prototype 1 | Prototype 2 | Prototype 3 | Prototype 4 |
|---|---|---|---|---|---|
| | Conc. (mg/mL) | 84.82 | 84.39 | 81 | 87.38 |
| | Purity, % | 99.4 | 99.4 | 99.4 | 99.4 |
| | Form change by XRPD | | Same to initial | | |
| 3 days at 4° C. | PSD (D90, nm) | 339.9 | 361.8 | 389.7 | 300.5 |
| | Appearance | Homogeneous suspension | Homogeneous suspension | Homogeneous suspension | Homogeneous suspension |
| | Conc. (mg/mL) | 86.53 | 82.43 | 89.83 | 82.85 |
| | Purity, % | 99.4 | 99.4 | 99.4 | 99.4 |
| | Form change by XRPD | | Same to initial | | |
| 3 days at RT | PSD (D90, nm) | 366.8 | 355.6 | 346.7 | 269.4 |
| | Appearance | Homogeneous suspension | Homogeneous suspension | Homogeneous suspension | Homogeneous suspension |
| | Conc. (mg/mL) | 88.04 | 85.39 | 90.09 | 84.67 |
| | Purity, % | 99.4 | 99.4 | 99.4 | 99.4 |
| | Form change by XRPD | | Same to initial | | |
| 7 days at 4° C. | PSD (D90, nm) | 321.5 | 391.0 | 353.8 | 315.9 |
| | Appearance | Homogeneous suspension | Homogeneous suspension | Homogeneous suspension | Homogeneous suspension |
| | Conc. (mg/mL) | 83.8 | 90.4 | 93.7 | 88.6 |
| | Purity, % | 98.5 | 98.5 | 98.5 | 98.5 |
| | Form change by XRPD | | Same to initial | | |
| 7 days at RT | PSD (D90, nm) | 371.3 | 422.4 | 380.4 | 263.3 |
| | Appearance | Homogeneous suspension | Homogeneous suspension | Homogeneous suspension | Homogeneous suspension |
| | Conc. (mg/mL) | 83.1 | 91.0 | 97.4 | 93.2 |
| | Purity, % | 98.5 | 98.5 | 98.5 | 98.5 |
| | Form change by XRPD | | Same to initial | | |

TABLE 17

Stability of Formula III nanosuspensions

| | | Prototype 1 | Prototype 2 | Prototype 3 | Prototype 4 |
|---|---|---|---|---|---|
| Initial | PSD (D90, nm) | 693 | 513.9 | 709.1 | 376.4 |
| | Appearance | Homogeneous suspension | Homogeneous suspension | Homogeneous suspension | Homogeneous suspension |
| | pH | 6.82 | 7.29 | 7.19 | 7.09 |
| | Conc. (mg/mL) | 52.5 | 54.3 | 51.0 | 55.8 |
| | Purity, % | 99.8 | 99.8 | 99.8 | 99.8 |
| | Form change by XRPD | | Same to initial | | |
| 3 days at 4° C. | PSD (D90, nm) | 1368.6 | 578.6 | 1037.0 | 400.8 |
| | Appearance | | Sedimentation at the bottom and became homogeneous suspension after agitation | | |
| | Conc. (mg/mL) | 51.9 | 48.0 | 48.0 | 49.2 |
| | Purity, % | 99.8 | 99.8 | 99.8 | 99.8 |
| | Form change by XRPD | Slight difference | Same to initial | Slight difference | Same to initial |
| 3 days at RT | PSD (D90, nm) | 1186.3 | 601.3 | 1321.4 | 422.9 |
| | Appearance | | Sedimentation at the bottom and became homogeneous suspension after agitation | | |

TABLE 17-continued

| Stability of Formula III nanosuspensions | | | | | |
|---|---|---|---|---|---|
| | | Prototype 1 | Prototype 2 | Prototype 3 | Prototype 4 |
| | Conc. (mg/mL) | 49.8 | 46.9 | 50.5 | 47.2 |
| | Purity, % | 99.8 | 99.8 | 99.8 | 99.8 |
| | Form change by XRPD | Slight difference | Same to initial | Slight difference | Same to initial |
| 7 days at 4° C. | PSD (D90, nm) | 1142.2 | 581.3 | 1366.5 | 416.4 |
| | Appearance | Sedimentation at the bottom and became homogeneous suspension after agitation | | | |
| | Conc. (mg/mL) | 47.83 | 49.01 | 45.95 | 52.12 |
| | Purity, % | 99.8 | 99.8 | 99.8 | 99.8 |
| | Form change by XRPD | Slight difference | Same to initial | Slight difference | Same to initial |
| 7 days at RT | PSD (D90, nm) | 1957.8 | 557.2 | 2513.1 | 424.5 |
| | Appearance | Sedimentation at the bottom and became homogeneous suspension after agitation | | | |
| | Conc. (mg/mL) | 49.68 | 49.71 | 47.68 | 52.46 |
| | Purity, % | 99.8 | 99.8 | 99.8 | 99.8 |
| | Form change by XRPD | Slight difference | Same to initial | Slight difference | Same to initial |

Example 10

Lyophilization Feasibility Study of Nanosuspensions Lyophilization

For both Formula II and Formula III, two batches of a nanosuspension (API and 1% Poloxamer 188/0.5% Tween® 80) were prepared. Batch 1 was API and % Poloxamer 188/0.5% Tween® 80; Batch 2 was API, 1% Poloxamer 188/0.5% Tween® 80, and mannitol in a 1:1 mass ratio as a bulking agent. Batch 1 and 2 were lyophilized. The lyophilized powder was then reconstituted in water and evaluated by XRPD, PSD, and HPLC. Results for Formula II and Formula III are shown in Table 18. XRPD results are shown in FIG. 22*a*, FIG. 22*b* FIG. 23*a*, and FIG. 23*b*.

TABLE 18

| Lyophilized powder reconstitution study and stability test | | | | | | | |
|---|---|---|---|---|---|---|---|
| | Formulation | Testing Items | Appearance | D90, nm | Conc., mg/mL | Purity | XRPD |
| Formula II | Lyophilization without mannitol | Initial | Homogenous suspension | 499.2 | 102.8 | 99.4 | Same to initial |
| | Lyophilization with mannitol | Initial | Homogenous suspension | 4711.2 | 94.1 | 99.4 | Same to initial |
| Formula III | Lyophilization without mannitol | Initial | Homogenous suspension | 634.8 | 46.84 | 99.8 | Same to initial |
| | | 3 days at RT | Homogenous suspension | 1020.4 | 50.45 | 99.8 | Same to initial |
| | | 3 days at 4° C. | Homogenous suspension | 855.7 | 49.42 | 99.7 | Same to initial |
| | Lyophilization with mannitol | Initial | Homogenous suspension with few particles | 3690.8 | 44.95 | 99.8 | Some change to initial nanosuspension |

Stability of Lyophilized Powders

Lyophilized powder for Formula II was evaluated for stability under two conditions for up to two weeks, results summarized in Table 19. After 1 week, lyophilized powders were found to be physically and chemically stable after reconstitution into water. After 2 weeks, particle size under two conditions increased after reconstitution into water.

TABLE 19

Stability of lyophilized powder after 1 week under RT and 4° C.

| Formulation | Testing Conditions | Appearance | D90, nm | Conc., mg/mL | Purity % | XRPD |
|---|---|---|---|---|---|---|
| Lyophilization without mannitol | Initial | Homogenous suspension | 499.2 | 102.8 | 99.4 | Same to initial |
| | 1 week at RT | | 394.2 | 108.9 | 99.4 | |
| | 1 week at 4° C. | | 453.8 | 102.7 | 99.4 | |
| | 2 weeks at RT | | 670.8 | 108.6 | 99.4 | |
| | 2 weeks at 4° C. | | 624.2 | 99.9 | 99.4 | |

What is claimed is:

1. An amorphous solid dispersion, comprising a compound of Formula I:

(I)

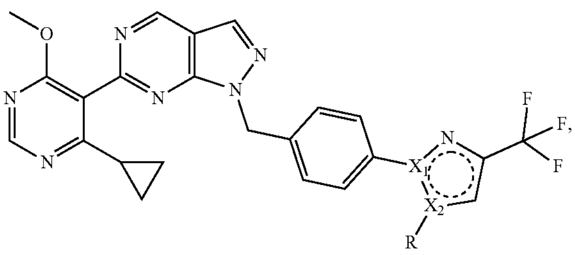

or a pharmaceutically acceptable salt thereof, wherein R is $C_{1-3}$ alkyl; and $X_1$ and $X_2$ are independently selected from the group consisting of N and C, wherein the compound is in a solid substantially amorphous form and is dispersed in a polymer.

2. The amorphous solid dispersion according to claim 1, wherein the compound is 6-(4-cyclopropyl-6-methoxypyrimidin-5-yl)-1-(4-(1-isopropyl-4-(trifluoromethyl)-1H-imidazol-2-yl) benzyl)-1H-pyrazolo[3,4-d]pyrimidine of Formula (II)

(II)

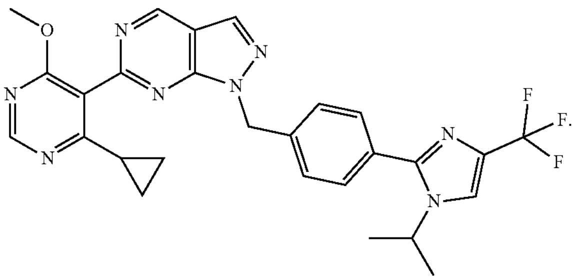

3. The amorphous solid dispersion according to claim 1, wherein the compound is 6-(4-cyclopropyl-6-methoxypyrimidin-5-yl)-1-(4-(5-methyl-3-(trifluoromethyl)-1H-pyrazol-1-yl) benzyl)-1H-pyrazolo[3,4-d]pyrimidine of Formula (III)

(III)

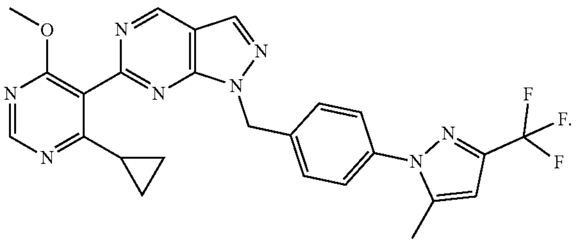

4. The amorphous solid dispersion according to claim 1, wherein the polymer is selected from the group consisting of polyvinyl pyrrolidone (PVP), polyvinyl alcohol (PVA), poly (ethylene glycol) (PEG), poly (ethylene oxide) (PEO), hydroxypropyl cellulose (HPC), hydroxypropyl methylcellulose (HPMC), copovidone, hydroxypropyl methylcellulose acetate succinate, methacrylic acid copolymer, polyacrylates and mixtures thereof.

5. The amorphous solid dispersion according to claim 1, wherein the polymer is selected from the group consisting of hydroxypropyl methylcellulose acetate succinate, hydroxypropyl methylcellulose, and methacrylic acid copolymer.

6. The amorphous solid dispersion according to claim 5, wherein the polymer is hydroxypropyl methylcellulose acetate succinate.

7. The amorphous solid dispersion according to claim 5, wherein the polymer is poly (methacrylic acid)-co-methyl methacrylate.

8. The amorphous solid dispersion according to claim 2, wherein the compound of Formula II is dispersed in hydroxypropyl methylcellulose acetate succinate.

9. The amorphous solid dispersion according to claim 2, wherein the compound of Formula II is dispersed in poly (methacrylic acid)-co-methyl methacrylate.

10. The amorphous solid dispersion according to claim 3, wherein the compound of Formula III is dispersed in hydroxypropyl methylcellulose acetate succinate.

11. The amorphous solid dispersion according to claim 3, wherein the compound of Formula III is dispersed in poly (methacrylic acid)-co-methyl methacrylate.

12. The amorphous solid dispersion according to claim 4, wherein the polymer is present in an amount of between about 40% and about 95% of the total weight of the solid dispersion.

13. The amorphous solid dispersion according to claim 5 wherein the polymer is present in an amount of between about 40% and about 95% of the total weight of the solid dispersion.

14. A pharmaceutical composition comprising a pharmaceutically acceptable carrier and a therapeutically effective amount of the amorphous solid dispersion according to claim 1.

15. The pharmaceutical composition according to claim 14, wherein said composition is in the form of a solid oral dosage form.

16. A method of treating cancer, comprising administering to a patient in need thereof a therapeutically effective amount of the amorphous solid dispersion according to claim 1.

17. The amorphous solid dispersion according to claim 1 wherein said solid dispersion is prepared by hot-melt extrusion, lyophilization or spray-drying.

18. A method of making a solid dispersion according to claim 1, comprising:

a) mixing the compound of Formula I and the polymer in a solvent to provide a feeder solution; and b) spray drying the feeder solution to provide the solid dispersion.

19. The method according to claim 18, wherein the compound of Formula I is provided as either the free base, salt, or solvate.

20. The method according to claim 18, wherein the solvent is selected from acetone, ethanol, methanol, or dichloromethane.

* * * * *